United States Patent
McRae et al.

(10) Patent No.: US 9,918,665 B2
(45) Date of Patent: *Mar. 20, 2018

(54) TRANSDERMAL PORATOR AND PATCH SYSTEM AND METHOD FOR USING SAME

(71) Applicant: Nitto Denko Corporation, Osaka (JP)

(72) Inventors: Stuart McRae, Decatur, GA (US); Wendy E. Bowerman, Lawrenceville, GA (US); Stephen Wilson Braun, Roswell, GA (US); Regina Spiehl, Norcross, GA (US); Bernadette Messier, Roswell, GA (US); David Farquhar, Commerce, GA (US); Erin Koch Henkel, New York, NY (US); Jeremiah Peter O'Leary, Chicago, IL (US); Mark James Fisher, Highland Park, IL (US); Uros Kascak, Dunwoody, GA (US); Loren J. Lantz, Tucker, GA (US); Zoran Novakovic, Irvine, CA (US); Jonathan Eppstein, Atlanta, GA (US)

(73) Assignee: Nitto Denko Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/147,263

(22) Filed: Jan. 3, 2014

(65) Prior Publication Data
US 2015/0190074 A1 Jul. 9, 2015

(51) Int. Cl.
*A61B 5/00* (2006.01)
*A61B 5/145* (2006.01)
(Continued)

(52) U.S. Cl.
CPC ...... *A61B 5/14503* (2013.01); *A61B 5/14532* (2013.01); *A61B 5/15* (2013.01);
(Continued)

(58) Field of Classification Search
CPC ............ A61B 5/14514; A61B 5/14532; A61B 5/14546; A61N 1/30; A61N 1/325; A61N 1/327
See application file for complete search history.

(56) References Cited

U.S. PATENT DOCUMENTS

| | | |
|---|---|---|
| 2,893,392 A | 7/1959 | Wagner |
| 3,551,554 A | 12/1970 | Herschler |

(Continued)

FOREIGN PATENT DOCUMENTS

| | | |
|---|---|---|
| AU | 2003213541 | 8/2003 |
| EP | 0 497 620 | 8/1992 |

(Continued)

OTHER PUBLICATIONS

"After bite's unique formula key to efficacy" news release (no author), Tender Corporation, Littleton, NH, Aug. 1994.
(Continued)

*Primary Examiner* — Eric Winakur
(74) *Attorney, Agent, or Firm* — King & Spalding LLP

(57) ABSTRACT

A transdermal permeant delivery of at least one permeant composition into a tissue membrane of a subject including a disposable substrate having at least a portion of a bottom surface of a first release liner connected to an upper surface of the substrate and a patch having a backing layer and a reservoir that is selectively removable from the top surface of the first release liner. In a connected position, a first portion of the backing layer of the patch is releaseably mounted to a top surface of the first release liner in spaced registration with a poration area of the substrate.

8 Claims, 25 Drawing Sheets

(51) Int. Cl.
  *A61B 5/15* (2006.01)
  *A61N 1/30* (2006.01)
  *A61N 1/32* (2006.01)
  *A61N 1/04* (2006.01)
  *A61M 37/00* (2006.01)

(52) U.S. Cl.
  CPC ............ *A61B 5/685* (2013.01); *A61N 1/0428* (2013.01); *A61N 1/303* (2013.01); *A61N 1/327* (2013.01); *A61M 2037/0007* (2013.01)

(56) References Cited

U.S. PATENT DOCUMENTS

| | | |
|---|---|---|
| 3,711,602 A | 1/1973 | Herschler |
| 3,711,606 A | 1/1973 | Herschler |
| 3,964,482 A | 6/1976 | Gerstel et al. |
| 4,340,048 A | 7/1982 | Eckenhoff |
| 4,522,622 A | 6/1985 | Peery et al. |
| 4,537,776 A | 8/1985 | Cooper |
| 4,557,943 A | 12/1985 | Rosler et al. |
| 4,758,081 A | 7/1988 | Barnes |
| 4,767,402 A | 8/1988 | Kost et al. |
| 4,775,361 A | 10/1988 | Jacques et al. |
| 4,820,720 A | 4/1989 | Sanders et al. |
| 4,844,098 A | 7/1989 | Mitchen |
| 4,855,298 A | 8/1989 | Yamada et al. |
| 4,860,743 A | 8/1989 | Abela |
| 4,863,970 A | 9/1989 | Patel et al. |
| 4,921,475 A | 5/1990 | Sibalis |
| 4,973,468 A | 11/1990 | Chiand et al. |
| 5,003,987 A | 4/1991 | Grinwald |
| 5,006,342 A | 4/1991 | Cleary et al. |
| 5,016,615 A | 5/1991 | Driller et al. |
| 5,019,034 A | 5/1991 | Weaver et al. |
| 5,041,109 A | 8/1991 | Abela |
| 5,092,864 A | 3/1992 | Hayes et al. |
| 5,115,805 A | 5/1992 | Bommannan et al. |
| 5,137,817 A | 8/1992 | Busta et al. |
| 5,139,023 A | 8/1992 | Stanley et al. |
| 5,165,418 A | 11/1992 | Tankovich |
| 5,169,389 A | 12/1992 | Kriesel |
| 5,171,215 A | 12/1992 | Flanagan |
| 5,190,558 A | 3/1993 | Ito |
| 5,215,520 A | 6/1993 | Slupot et al. |
| 5,223,219 A | 6/1993 | Subramanian et al. |
| 5,224,928 A | 7/1993 | Sibalis et al. |
| 5,226,907 A | 7/1993 | Tankovich |
| 5,231,975 A | 8/1993 | Bommannan et al. |
| 5,246,437 A | 9/1993 | Abela |
| 5,250,023 A | 10/1993 | Lee et al. |
| 5,267,985 A | 12/1993 | Shimada et al. |
| 5,273,525 A | 12/1993 | Hofmann |
| 5,279,544 A | 1/1994 | Gross et al. |
| 5,318,514 A | 6/1994 | Hofmann |
| 5,323,769 A | 6/1994 | Bommannan et al. |
| 5,328,453 A | 7/1994 | Sibalis |
| 5,342,355 A | 8/1994 | Long |
| 5,362,307 A | 11/1994 | Guy et al. |
| 5,380,272 A | 1/1995 | Gross |
| 5,421,816 A | 6/1995 | Lipkovker |
| 5,423,803 A | 6/1995 | Tankovich et al. |
| 5,425,728 A | 6/1995 | Tankovich |
| 5,427,585 A | 6/1995 | Bettinger |
| 5,445,609 A | 8/1995 | Lattin |
| 5,445,611 A | 8/1995 | Eppstein et al. |
| 5,458,140 A | 10/1995 | Eppstein et al. |
| 5,459,127 A | 10/1995 | Feigner et al. |
| 5,462,520 A | 10/1995 | Hoffmann |
| 5,547,467 A | 8/1996 | Pliquett et al. |
| 5,548,140 A | 8/1996 | Nguyen et al. |
| 5,554,153 A | 9/1996 | Costello et al. |
| 5,580,859 A | 12/1996 | Felger et al. |
| 5,582,586 A | 12/1996 | Tachibana et al. |
| 5,611,806 A | 3/1997 | Jang |
| 5,651,768 A | 7/1997 | Sibalis |
| 5,697,901 A | 12/1997 | Eriksson |
| 5,713,845 A | 2/1998 | Tankovich |
| 5,749,847 A | 5/1998 | Zewert et al. |
| 5,752,949 A | 5/1998 | Tankovich et al. |
| 5,801,057 A | 9/1998 | Smart et al. |
| 5,817,089 A | 10/1998 | Tankovich et al. |
| 5,879,326 A | 3/1999 | Godshall et al. |
| 5,882,317 A | 3/1999 | Saito et al. |
| 5,885,211 A | 3/1999 | Eppstein et al. |
| 5,925,035 A | 7/1999 | Tankovich |
| 5,947,921 A | 9/1999 | Johnson et al. |
| 5,983,136 A | 11/1999 | Kamen |
| 6,013,318 A | 1/2000 | Hunt et al. |
| 6,022,316 A * | 2/2000 | Eppstein et al. ............... 600/309 |
| 6,027,459 A | 2/2000 | Shain et al. |
| 6,048,337 A | 4/2000 | Svedman |
| 6,050,988 A | 4/2000 | Zuck |
| 6,056,738 A | 5/2000 | Marchitto et al. |
| 6,071,249 A | 6/2000 | Cunningham et al. |
| 6,071,251 A | 6/2000 | Cunningham et al. |
| 6,083,196 A | 7/2000 | Trautman et al. |
| 6,117,290 A | 9/2000 | Say et al. |
| 6,138,044 A | 10/2000 | Svedman |
| 6,142,939 A | 11/2000 | Eppstein et al. |
| 6,148,232 A | 11/2000 | Avrahami |
| 6,173,202 B1 | 1/2001 | Eppstein |
| 6,183,434 B1 | 2/2001 | Eppstein |
| 6,219,574 B1 | 4/2001 | Cormier et al. |
| 6,230,051 B1 | 5/2001 | Cormier et al. |
| 6,247,485 B1 | 6/2001 | Rossi et al. |
| 6,251,083 B1 | 6/2001 | Yum et al. |
| 6,290,991 B1 | 9/2001 | Roser et al. |
| 6,334,856 B1 | 1/2002 | Allen et al. |
| 6,352,506 B1 | 3/2002 | Eppstein et al. |
| 6,451,240 B1 | 9/2002 | Sherman et al. |
| 6,508,785 B1 | 1/2003 | Eppstein |
| 6,527,716 B1 | 3/2003 | Eppstein |
| 6,653,114 B2 | 11/2003 | Walters |
| 6,659,982 B2 | 12/2003 | Douglas |
| 6,692,456 B1 | 2/2004 | Eppstein et al. |
| 6,730,028 B2 | 5/2004 | Eppstein et al. |
| 6,887,202 B2 * | 5/2005 | Currie et al. .................. 600/309 |
| 6,906,540 B2 | 6/2005 | McQuade |
| 7,041,057 B1 | 5/2006 | Faupel et al. |
| 7,045,069 B2 | 5/2006 | Ozeryansky |
| 7,048,723 B1 | 5/2006 | Frazier |
| 7,070,590 B1 | 7/2006 | Santini |
| 7,108,681 B2 | 9/2006 | Gartstein |
| 7,131,987 B2 | 11/2006 | Sherman |
| 7,141,034 B2 | 11/2006 | Eppstein et al. |
| 7,344,499 B1 * | 3/2008 | Prausnitz et al. ............. 600/309 |
| 7,392,080 B2 | 6/2008 | Eppstein et al. |
| D605,775 S | 12/2009 | Koch et al. |
| 7,758,561 B2 | 7/2010 | Eppstein |
| 8,116,860 B2 | 2/2012 | Messier et al. |
| 2002/0010414 A1 | 1/2002 | Coston |
| 2002/0038101 A1 | 3/2002 | Avrahami et al. |
| 2003/0092982 A1 | 5/2003 | Eppstein |
| 2003/0225360 A1 | 12/2003 | Eppstein |
| 2004/0039342 A1 | 2/2004 | Eppstein |
| 2004/0158137 A1 | 8/2004 | Eppstein |
| 2004/0220456 A1 | 11/2004 | Eppstein |
| 2005/0165393 A1 | 7/2005 | Eppstein |

FOREIGN PATENT DOCUMENTS

| | | |
|---|---|---|
| EP | 0 506 632 | 9/1992 |
| EP | 0 514 258 | 11/1992 |
| GB | 2 153 233 | 8/1985 |
| GB | 2 221 393 | 2/1990 |
| JP | 2004-505652 A | 12/2000 |
| WO | WO 92/00106 | 1/1992 |
| WO | WO 93/07801 | 4/1993 |
| WO | WO 93/20745 | 10/1993 |
| WO | WO 94/08655 | 4/1994 |
| WO | WO 94/09713 | 5/1994 |
| WO | WO 95/10223 | 4/1995 |
| WO | WO 96/00110 | 1/1996 |
| WO | WO 96/17648 | 6/1996 |

(56) References Cited

FOREIGN PATENT DOCUMENTS

| WO | WO 96/41657 | 12/1996 |
|---|---|---|
| WO | WO 97/04832 | 2/1997 |
| WO | WO 97/07734 | 3/1997 |
| WO | WO 98/00193 | 1/1998 |
| WO | WO 98/22719 | 5/1998 |
| WO | WO 98/29134 | 7/1998 |
| WO | WO 99/29364 | 6/1999 |
| WO | WO 99/40848 | 8/1999 |
| WO | WO 99/43350 | 9/1999 |
| WO | WO 99/44507 | 9/1999 |
| WO | WO 99/44508 | 9/1999 |
| WO | WO 99/44637 | 9/1999 |
| WO | WO 99/44638 | 9/1999 |
| WO | WO 99/44678 | 9/1999 |
| WO | WO 00/03758 | 1/2000 |
| WO | WO 00/04821 | 2/2000 |
| WO | WO 00/04832 | 2/2000 |
| WO | WO 00/15102 | 3/2000 |
| WO | WO 00/27473 | 5/2000 |
| WO | WO 00/74767 | 12/2000 |
| WO | WO 00/074767 | 12/2000 |
| WO | WO 03/039620 | 5/2003 |
| WO | WO 03/077970 | 9/2003 |
| WO | WO 06/131931 | 12/2006 |

OTHER PUBLICATIONS

Brusilow et al "Ammonia Secretion in Sweat," *Am. J Physiology*, vol. 214, No. 3:513-517.

Gustin et al. "Effects of Atmospheric Ammonia on Pulmonary Hemodynamic and Vascular Permeability in Pigs: Interactions with Endiotoxins," *Toxicology and Applied Pharmacology* 125:17-26 (1994).

Jacques et al. "Controlled Removal of Human Stratum Corneum by Pulsed Laser," *J. Invest. Dermatol.* 88:88-93 (1987).

Lane et al., "Ultraviolet-laser Ablation of Skin," *Arch Dermatol.* 121:609-617 (1985).

Matsumoto et al. "Substance P Antagonist Does Not Block the Stimulation of Rapidly Adapting Pulmonary Stretch Receptors by Ammonia", *Lung* 172:31-45 (1994).

Matsumoto "Effects of ammonia and histamine on lung irritant receptors in the rabbit," *Respiratory Physiology* 77:301-308 (1989).

McClung et al. "Early Changes in the Permeability of the Blood-Brain Barrier Produced by Toxins Associated with Liver Failure," *Pediatric Research* 28 No. 3 227-231 (1990).

Pohl et al. "Microjet assisted dye-enhanced diode laser ablation of cartilaginous tissue" *SPIE* vol. 2134A of *Laser-Tissue Interaction* (1994) at pp. 1326-1328.

Santus et al. "Transdermal enhancer patent literature" *J. Control Release* 25:1-20 (1993).

Zaki et al. "Potential Toxins of acute liver failure and their effects on blood brain permeability," *Experientia* 39, Birkhäuser Verlag, CH-4010 Basel/Switzerland:988-991 (1983).

Ziylan et al. "Changes in the permeability of the blood brain barrier in acute hyperammonemia. Effect of dexamethasone" *Mol Chem Neurpathol* 20:203-218 (1993).

Ueda et al. "Skin penetration-enhancing effect of drugs by phonophoresis" *J of Controlled Release*. vol. 37:291-297 (1995).

Extended European Search Report, European application No. 16207154.2.

1st Office Action (original) in corresponding Japanese application No. 2016-196372 (from PCT/US2008/051679).

1$^{st}$ Office Action (machine translation) in corresponding Japanese application No. 2016-196372 (from PCT/US2008/051679).

1st Office Action in corresponding Canadian application No. 2925191 (from PCT/US2008/051679).

International Search Report in PCT/US2008/051679.

\* cited by examiner

TRANSDERMAL PORATOR AND PATCH SYSTEM AND METHOD FOR USING SAME

CROSS REFERENCE TO RELATED APPLICATIONS

This patent application is a divisional application of U.S. patent application Ser. No. 13/272,592, titled Transdermal Porator and Patch System and Method for Using Same, filed Oct. 13, 2011, which claims priority under 35 U.S.C. § 120 to U.S. patent application Ser. No. 12/017,996, titled Transdermal Porator and Patch System and Method for Using Same, filed Jan. 22, 2008, and granted on Feb. 14, 2012, as U.S. Pat. No. 8,116,860, which claims priority under 35 U.S.C. § 119 to U.S. Provisional Application No. 60/886,039, filed on Jan. 22, 2007. U.S. patent application Ser. No. 13/272,592 is also a continuation-in-part of U.S. patent application Ser. No. 10/384,763, filed on Mar. 11, 2003, which also claims priority to U.S. Provisional Application No. 60/363,022, filed on Mar. 11, 2002. These applications are herein incorporated by reference in their entireties.

FIELD OF THE INVENTION

This invention relates to a system and method for transdermal delivery of drugs or other permeants through the skin of a subject. More particularly, this invention relates to a system and method for the creation of small holes or perforations or micropores in a biological membrane of the subject and the subsequent transdermal delivery of drugs or other permeants into the subject via the formed micropores.

BACKGROUND

The stratum corneum is chiefly responsible for the barrier properties of skin. Thus, it is this layer that presents the greatest barrier to transdermal flux of drugs or other molecules into the body and of analytes out of the body. The stratum corneum, the outer horny layer of the skin, is a complex structure of compact keratinized cell remnants separated by lipid domains. Compared to the oral or gastric mucosa, the stratum corneum is much less permeable to molecules either external or internal to the body. The stratum corneum is formed from keratinocytes, which comprise the majority of epidermal cells that lose their nuclei and become corneocytes. These dead cells comprise the stratum corneum, which has a thickness of only about 10-30 microns and protects the body from invasion by exogenous substances and the outward migration of endogenous fluids and dissolved molecules. The stratum corneum is continuously renewed by shedding of corneum cells during desquamination and the formation of new corneum cells by the keratinization process. Historically, the majority of drugs have been delivered orally or by injection. However, neither the oral or injection route is well-suited for continual delivery of drugs over an extended period of time. Further, the injection method of administration is inconvenient and uncomfortable; additionally, needles continue to pose a hazard after their use. Therefore, transdermal drug delivery to the body has been a popular and efficacious method for delivering a limited number of permeants into an organism.

To enhance transdermal drug delivery, there are known methods for increasing the permeability of the skin to drugs. For example, U.S. Pat. No. 5,885,211 is directed to thermal microporation techniques and devices to form one or more micropores in a biological membrane and methods for selectively enhancing outward flux of analytes from the body or the delivery of drugs into the body. PCT WO 00/03758, published Jan. 27, 2000, is directed to methods and apparatus for forming artificial openings in a selected area of a biological membrane using a pyrotechnic element that, when triggered, explodes in a controlled fashion so that the micro-explosion produces the artificial opening in the biological membrane to a desired depth and diameter. PCT WO98/29134, published Jul. 9, 1998 discloses a method of enhancing the permeability of a biological membrane, such as the skin of an animal, using microporation and an enhancer such as a sonic, electromagnetic, mechanical, thermal energy or chemical enhancer. Methods and apparatus for delivery or monitoring using microporation also are described in PCT WO 99/44637, published Sep. 10, 1999; U.S. Pat. No. 6,022,316; PCT WO 99/44508, published Sep. 10, 1999; PCT WO 99/44507, published Sep. 10, 1999; PCT WO 99/44638, published Sep. 10, 1999; PCT WO 00/04832, published Feb. 3, 2000; PCT WO 00/04821, published Feb. 3, 2000; and PCT WO 00/15102, published Mar. 23, 2000. Applicants would note that all publications, patents and patent applications referred to herein, such as those above, are incorporated herein by reference in their entirety.

There remains a need for improved methods and devices for transdermal delivery of permeants such as, for example, drugs, bio-active compositions, and the like.

SUMMARY

According to one embodiment of the invention, a system and method for transdermal permeant delivery of at least one permeant into a tissue membrane of a subject is provided. In one aspect, the transdermal permeant delivery system comprises a disposable substrate, a first release liner, and a patch that is selectively removable from a top surface of the first release liner. The substrate defines a poration area that is configured for forming micropores in the tissue membrane of the subject. In another aspect, at least a portion of a bottom surface of the first release liner is connected to an upper substrate surface of the substrate. In a further exemplary aspect, the patch comprises a backing layer and a reservoir mounted thereon a portion of a lower surface of the backing layer that is configured for releaseably containing the at least one permeant. In a connected position, in which the patch is mounted to the first release liner, a first portion of the backing layer is releaseably mounted thereto the top surface of the first release liner in spaced registration with the poration area of the substrate. In another aspect, a second portion of the backing layer is folded back about a fold into a folded position when the patch is in the connected position such that the lower surface of the second portion of the backing layer faces outwardly away from the upper substrate surface of the substrate.

Other apparatus, methods, and aspects and advantages of the invention will be discussed with reference to the Figures and to the detailed description of the preferred embodiments.

BRIEF DESCRIPTION OF THE FIGURES

The accompanying drawings, which are incorporated in and constitute a part of this specification, illustrate several aspects described below and together with the description, serve to explain the principles of the invention. Like numbers represent the same elements throughout the figures.

DETAILED DESCRIPTION OF THE INVENTION

Figure 1:
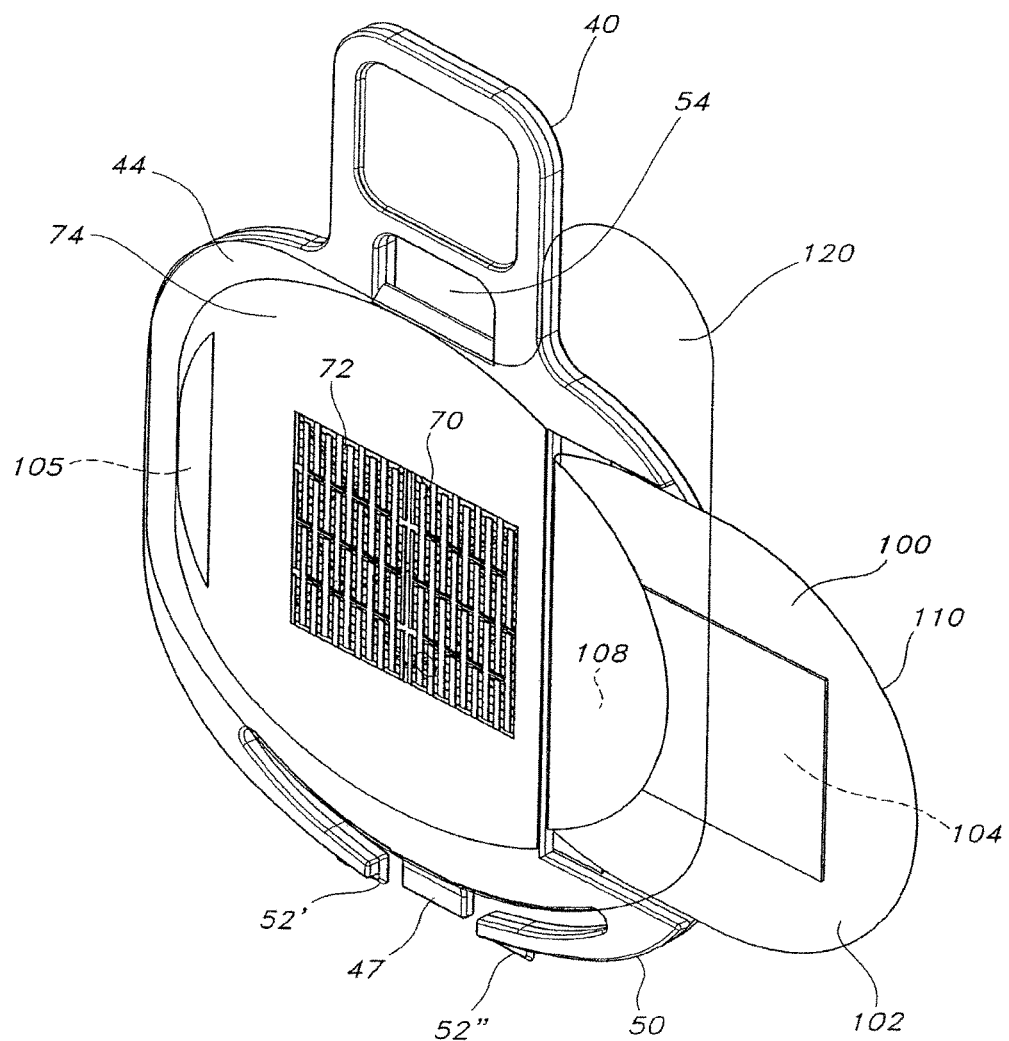
FIG. 1 is a perspective view of a transdermal permeant delivery system showing a first embodiment of a transdermal patch of the present invention mounted thereon an embodiment of a disposable substrate.
Figure 2:
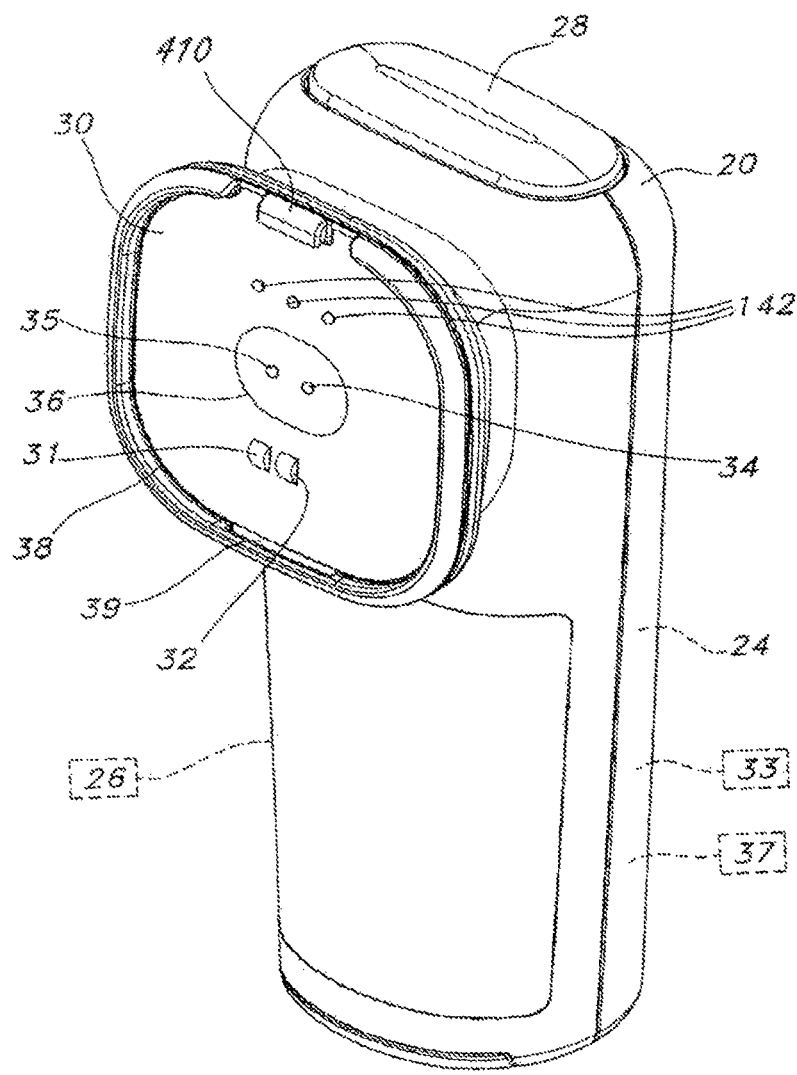
FIG. 2 is a perspective view of an exemplary embodiment of an applicator of the present invention.
Figure 3:
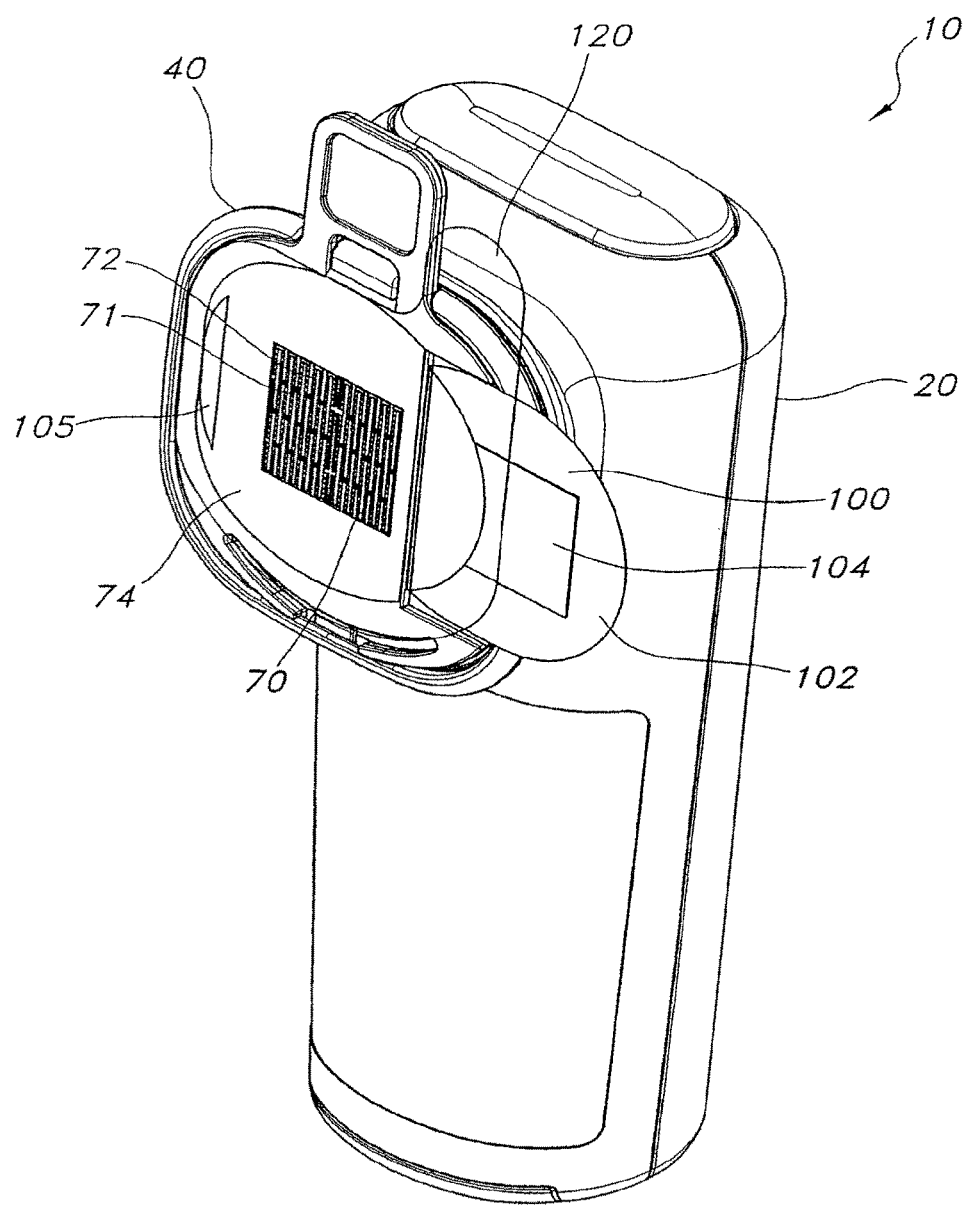
FIG. 3 is perspective view of the delivery system of FIG. 1 releasably connected to the applicator of FIG. 2.

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an," and "the" include plural referents unless the context clearly dictates otherwise. Thus, for example, reference to "a filament" can include two or more such filaments unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

As used herein, a "tissue membrane" can be any one or more epidermal layers of a subject. For example, in one aspect, the tissue membrane is a skin layer that includes the outermost layer of the skin, i.e., the stratum corneum. In an alternative aspect, a skin layer can include one or more backing layers of the epidermis, commonly identified as stratum granulosum, stratum malpighii, and stratum germinativum layers. It will be appreciated by one of ordinary skill in the art that there is essentially little or no resistance to transport or to absorption of a permeant through the backing layers of the epidermis. Therefore, in one aspect of the present invention, an at least one formed pathway in a skin layer of a subject is a pathway in the stratum corneum layer of a subject. Further, as used herein, "stratum corneum" refers to the outermost layer of the skin, consisting of from about 15 to about 20 layers of cells in various stages of drying out. The stratum corneum provides a barrier to the loss of water from inside the body to the external environment and from attack from the external environment to the interior of the body. Still further, as used herein, "tissue membrane" can refer to an aggregate of cells of a particular kind, together with their intercellular substance, that forms a structural material. At least one surface of the tissue membrane must be accessible to the device. As noted above, the preferred tissue membrane is the skin. Other tissues suitable for use with this invention include mucosal tissue and soft organs.

As used herein, the term, "subcutaneous fluid" can include, without limitation, moisture, plasma, blood, one or more proteins, interstitial fluid, and any combination thereof. In one aspect, a subcutaneous fluid according to the instant invention is a moisture source comprising water.

As used herein, "poration," "microporation," or any such similar term means the formation of a small hole or crevice (subsequently also referred to as a "micropore") in or through the tissue or biological membrane, such as skin or mucous membrane, or the outer layer of an organism to lessen the barrier properties of this biological membrane for the passage of at least one permeant from one side of the biological membrane to the other for select purposes. Preferably the hole or "micropore" so formed is approximately 1-1000 microns in diameter and extends into the biological membrane sufficiently to break the barrier properties of the stratum corneum without adversely affecting the underlying tissues. It is to be understood that the term "micropore" is used in the singular form for simplicity, but that the device of the present invention may form multiple artificial openings. Poration could reduce the barrier properties of a biological membrane into the body for selected purposes, or for certain medical or surgical procedures. For the purposes of this application, "poration" and "microporation" are used interchangeably and mean the same thing.

A "microporator" or "porator" is a component for a microporation device capable of microporation. Examples of a microporator or porator include, but are not limited to, a filament capable of conductively delivering thermal energy via direct contact to a biological membrane to cause the ablation of some portion of the membrane deep enough to form a micropore, an optically heated topical dye/absorber layer, an electromechanical actuator, a microlancet, an array of microneedles or lancets, a sonic energy ablator, a laser ablation system, a high-pressure fluid jet puncturer, and the like. As used herein, "microporator" and "porator" are used interchangeably.

As used herein, "penetration enhancement" or "permeation enhancement" means an increase in the permeability of the biological membrane to a drug, bio-active composition, or other chemical molecule, compound, particle or substance (also called "permeant"), i.e., so as to increase the rate at which the drug, bio-active composition, or other chemical molecule, compound or particle permeates the biological membrane.

As used herein, "enhancer," "chemical enhancer," "penetration enhancer," "permeation enhancer," and the like includes all enhancers that increase the flux of a permeant, analyte, or other molecule across the biological membrane, and is limited only by functionality. In other words, all cell envelope disordering compounds and solvents and any other chemical enhancement agents are intended to be included. Additionally, all active force enhancer technologies such as the application of sonic energy, mechanical suction, pressure, or local deformation of the tissues, iontophoresis or electroporation are included. One or more enhancer technologies may be combined sequentially or simultaneously. For example, a chemical enhancer may first be applied to permealize the capillary wall and then an iontophoretic or sonic energy field may be applied to actively drive a permeant into those tissues surrounding and comprising the capillary bed.

As used herein, "transdermal" means passage of a permeant into and through the biological membrane.

As used herein, the term "permeant," "drug," "permeant composition," or "pharmacologically active agent" or any other similar term are used interchangeably to refer to any chemical or biological material or compound suitable for transdermal administration by the methods previously known in the art and/or by the methods taught in the present invention, that induces a desired biological or pharmacological effect, which may include but is not limited to (1) having a prophylactic effect on the organism and preventing an undesired biological effect such as an infection, (2) alleviating a condition caused by a disease, for example, alleviating pain or inflammation, and/or (3) either alleviating, reducing, or completely eliminating the disease from the organism. The effect may be local, such as providing for a local anesthetic effect, or it may be systemic. Such substances include broad classes of compounds normally delivered into the body, including through body surfaces and membranes, including skin. In general, for example and not meant to be limiting, such substances can include any drug, chemical, or biological material that induces a desired biological or pharmacological effect. To this end, in one aspect, the permeant can be a small molecule agent. In another aspect, the permeant can be a macromolecular agent. In general, and without limitation, exemplary permeant include, but are not limited to, anti-infectives such as antibiotics and antiviral agents; analgesics and analgesic combinations; anorexics; antihelminthics; antiarthritics; antiasthmatic agents; anticoagulant; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including potassium and calcium channel blockers, beta-blockers, alpha-blockers, and antiarrhythmics; antihypertensives; diuretics and antidiuretics; vasodilators including general coronary, peripheral, and cerebral; central nervous system stimulants; vasoconstrictors; cough and cold preparations, including decongestants; hormones such as estradiol and other steroids, including corticosteroids; hypnotics; immunosuppressives; muscle relaxants; parasympatholytics; psychostimulants; sedatives; and tranquilizers.

The devices and methods of the instant invention can also be used to transdermally deliver peptides, polypeptides, proteins, or other macromolecules known to be difficult to convey across the skin with existing conventional techniques because of their size. These macromolecular substances typically have a molecular weight of at least about 300 Daltons, and more typically, in the range of about 300 to 40,000 Daltons. Examples of polypeptides and proteins which may be delivered in accordance with the present invention include, without limitation, antibodies, LHRH, LHRH analogs (such as goserelin, leuprolide, buserelin, triptorelin, gonadorelin, napharelin and leuprolide), GHRH, GHRF, insulin, insulinotropin, calcitonin, octreotide, endorphin, TRH, NT-36 (chemical name: N-[[(s)-4-oxo-2-azetidinyl]-carbonyl]-L-histidyl-L-prolinamide), liprecin, pituitary hormones (e.g., HGH, HMG, HCG, desmopressin acetate, etc.), follicle luteoids, alpha-ANF, growth factor such as releasing factor (GFRF), beta-MSH, GH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hirudin and hirudin analogs such as hirulog, hyaluronidase, interleukin-2, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, antidiuretic hormone antagonists, bradykinin antagonists, CD4, ceredase, CSI's, enkephalins, FAB fragments, IgE peptide suppressors, IGF-1, neurotrophic factors, colony stimulating factors, parathyroid hormone and agonists, parathyroid hormone antagonists, prostaglandin antagonists, cytokines, lymphokines, pentigetide, protein C, protein S, renin inhibitors, thymosin alpha-1, thrombolytics, TNF, GCSF, EPO, PTH, heparin having a molecular weight from 3000 to 12,000 Daltons, vaccines, vasopressin antagonist analogs, interferon-alpha, -beta, and -gamma, alpha-1 antitrypsin (recombinant), and TGF-beta genes; peptides; polypeptides; proteins; oligonucleotides; nucleic acids; and polysaccharides.

Further, as used herein, "peptide", means peptides of any length and includes proteins. The terms "polypeptide" and "oligopeptide" are used herein without any particular intended size limitation, unless a particular size is otherwise stated. Exemplary peptides that can be utilized include, without limitation, oxytocin, vasopressin, adrenocorticotrophic hormone, epidermal growth factor, prolactin, luliberin or luteinising hormone releasing hormone, growth hormone, growth hormone releasing factor, insulin, somatostatin, glucagon, interferon, gastrin, tetragastrin, pentagastrin, urogastroine, secretin, calcitonin, enkephalins, endorphins, angiotensins, renin, bradykinin, bacitracins, polymixins, colistins, tyrocidin, gramicidines, and synthetic analogues, modifications and pharmacologically active fragments thereof, monoclonal antibodies and soluble vaccines. It is contemplated that the only limitation to the peptide or protein drug which may be utilized is one of functionality.

Examples of peptide and protein drugs that contain one or more amino groups include, without limitation, anti-cancer agents, antibiotics, anti-emetic agents, antiviral agents, anti-inflammatory and analgesic agents, anesthetic agents, anti-ulceratives, agents for treating hypertension, agents for treating hypercalcemia, agents for treating hyperlipidemia, etc., each of which has at least one primary, secondary or tertiary amine group in the molecule, preferably, peptides, proteins or enzymes such as insulin, calcitonin, growth hormone, granulocyte colony-stimulating factor (G-CSF), erythropoietin (EPO), bone morphogenic protein (BMP), interferon, interleukin, platelet derived growth factor (PDGF), vascular endothelial growth factor (VEGF), fibroblast growth factor (FGF), nerve growth factor (NGF), urokinase, etc. can be mentioned. Further examples of protein drugs include, without limitation, insulin, alpha-, beta-, and gamma-interferon, human growth hormone, alpha- and beta-1-transforming growth factor, granulocyte colony stimulating factor (G-CSF), granulocyte macrophage colony stimulating factor (G-MCSF), parathyroid hormone (PTH), human or salmon calcitonin, glucagon, somatostatin, vasoactive intestinal peptide (VIP), and LHRH analogs.

As used herein, an "effective" amount of a pharmacologically active agent means an amount sufficient to provide the desired local or systemic effect and performance at a reasonable benefit/risk ratio attending any medical treatment. An "effective" amount of a permeation or chemical enhancer as used herein means an amount selected so as to provide the desired increase in biological membrane permeability, the desired depth of penetration, rate of administration, and amount of drug delivered.

Embodiments of the present invention are described below with reference to block diagrams and flowchart illustrations of methods, apparatuses (i.e., systems) and computer program products according to an embodiment of the invention. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Referring to the figures, the present invention for a transdermal permeant delivery system comprises a system and method for painlessly creating microscopic holes, i.e., micropores, from about 1 to about 1000 microns in diameter in the biological membrane of a subject, such as, for example, and not meant to be limiting, the stratum corneum of human skin. The system allows for a rapid and painless method of eliminating the barrier function of the stratum corneum to facilitate the transcutaneous transport of therapeutic substances into the body via the formed micropores when applied topically to the poration site.

In one embodiment, the transdermal permeant delivery system 10 comprises an applicator 20, a substrate 40 that comprises a portion of a means for forming at least one micropore, and a registerable patch 100 that is configured to contain at least one permeant. In one aspect, the applicator 20 comprises a body 22 that defines an interior cavity 24 and a portion of the means for forming at least one micropore. In this exemplary aspect, the portion of the means for forming at least one micropore of the applicator 20 can comprise a controller 26 comprising driving electronics such as, for example, an electrical circuit board and a power source, such as, for example a battery. In this aspect, the controller 26 is positioned within the interior cavity of the body. In an exemplary aspect, the controller is configured to provide a stimulus to the means for forming the at least one micropore that is positioned therein the substrate 40 to initiate formation of the at least one micropore upon user command. In alternative aspects, the stimulus can comprise an electrical driving current, such as, for example and not meant to be limiting, a pulsed electrical current, a RF pulse, and the like, when an actuator button 28 is actuated by a user of the system. Optionally, the controller 26 is configured to provide a thermal pulse when the actuator button is pressed.

In a further aspect, the applicator 20 comprises an interface 30 that is configured for securely and releasably mounting the substrate 40 thereto. The applicator interface can comprise an anode 31 and a cathode 32 that are in electrical communication with respective portions of the means for forming the at least one micropore when the substrate is mounted to the interface. In one aspect, the anode and cathode extend outwardly from the interface 30 of the applicator. Optionally, the anode and the cathode can be pins that extend from the interface of the applicator to from two exposed electrodes.

In another aspect, the applicator 20 can further comprise a source of vacuum 33, such as, for example, a vacuum pump. In this aspect, it is contemplated that the interface 30 defines a first port 34 that is in communication with the source of vacuum. Further, the interface 30 of the applicator 20 can comprise a gasket 36 mounted about the first port of the interface. Optionally, the interface can define a second port 35 that is in communication with a vacuum sensor 37. In this aspect, it is contemplated that the respective first and second ports are surrounded by the gasket.

The substrate 40 of the system can comprise an upper substrate surface 42, a lower substrate surface 44 and a defined poration area 46. In one aspect, the poration area defines an area on the upper substrate surface 42 upon which at least a portion of a means for forming at least one micropore is positioned. Thus, in operation, the micropores formed by the system of the present invention will be confined to those portions of the tissue membrane that underlie the poration area of the substrate.

In one aspect, the substrate 40 can have at least one male tab 46 that extends outwardly from a peripheral edge portion 50 of the substrate. Further, a portion of the peripheral edge of the substrate can comprise at least one bias element 52. In one exemplary aspect, the at least one bias element 52 comprises at least one partial leaf spring member 52', 52" that is positioned to articulate generally within the plane of the substrate. Optionally, the at least one male tab can be positioned on the peripheral edge of the substrate such that is positioned generally between a pair of bias elements. In a further aspect, the substrate defines an opening 54 that is positioned generally opposite to the at least one bias element and, optionally, generally opposite to the at least one male tab 46. In this aspect, the interface 30 of the applicator 20 comprises a lip 38 and at least one slot 39 that are configured to operatively engage the respective at least one bias element and the at least one male tab of the substrate. In a further aspect, the interface 30 comprises a male finger 200 that extends outwardly from the face of the interface. In this aspect, the male finger can be positioned generally opposite to the at least one slot 39. One skilled in the art will appreciate that the cooperative relationship between the at least one bias element 52, the at least one male tab 46, and the opening 54 of the substrate 40 and the lip 38, the at least one slot 39, and the male finger 200 of the interface facilitates a user's ability to easily mount and remove the substrate from the interface of the applicator.

In a further aspect, the substrate 40 defines a conduit 56 that extends between the lower and upper substrate surfaces. In this aspect, one open end 58 of the conduit is defined on the poration area 46 that is formed on the upper substrate surface 42 of the substrate. In another aspect, the substrate 40 defines at least one channel 60 on the upper substrate surface 42. It is contemplated that the at least one channel will be formed therein the poration area of the substrate. In this aspect, the at least one channel 60 is in fluid communication with the conduit. When the substrate 40 is mounted to the interface 30, the open end 59 of the conduit defined on the lower substrate surface 44 is configured to be positioned in fluid communication with the port 34 of the interface. In one operational aspect and as one skilled in the art will appreciate, the gasket 36 helps to form a fluid tight seal between the respective first and second ports of the applicator 20 and the conduit 56 of the substrate when the source of vacuum 33 is actuated.

Optionally, the substrate 40 can comprises a ridge 41 defined on the upper substrate surface 42 that, in one embodiment, extends generally outwardly from the upper substrate surface. In one aspect, the ridge extends peripherally about at least a portion of the poration area of the substrate. In a further exemplary aspect, the ridge is continuous and substantially surrounds the poration area. In use, the exemplary ridge can act as a sealing member formed between the biological membrane and the substrate when the source of vacuum is actuated and communicated to the poration area via the conduit and the channels. Thus, the ridge can aid in minimizing the amount of vacuum required to draw the biological membrane into substantial conformal contact with the means for forming at least one micropore that is positioned therein the poration area.

In a further aspect, the substrate 40 can optionally define a female depression 48 on a portion of the upper substrate surface that extends from a portion of the peripheral edge of the substrate inwardly toward the poration area of the substrate. In this aspect, the edges of the female depression in the upper substrate surface can form the ridge 41. Optionally, at least a portion of the ridge 41 of the female depression 48 can be spaced a predetermined distance from the poration area 46 of the substrate. In another aspect, the female depression can be substantially planar.

In alternative aspects, the means for forming at least one micropore comprises at least one filament that can comprise, for example and not meant to be limiting, a wire conductor, a deposited conductive material, a machined conductive material, a laser conductive material, an adhesive foil, an electroplated material, a screen-printed material, and etched conductive material, and the like. In a further aspect the at least one filament can comprise a filament array having a plurality of filaments. Various methodologies for forming filament arrays suitable for use in the system of the present invention are described in U.S. Pat. Nos. 6,692,456 and 7,141,034 to Eppstein, et al., all of which are incorporated herein by reference in their entirety.

Optionally, the means for forming at least one micropore can comprise, for example and not meant to be limiting, a filament capable of conductively delivering thermal energy via direct contact to the tissue biological membrane to cause the ablation of some portion of that membrane deep enough to form the micropore, a probe element capable of delivering electrical energy via direct contact to a tissue membrane to cause ablation of some portion of said membrane deep enough to form the micropore, an electro-mechanical applicator, a microlancet, an array of micro-needles or lancets, a sonic energy ablator, a laser ablation system, and a high-pressure fluid jet puncturer as described in U.S. Pat. No. 5,885,211 to Eppstein, et al., U.S. Pat. No. 6,527,716 to Eppstein, et al., and pending U.S. Published application Ser. No. 11/081,448, all of which are incorporated herein by reference in their entirety.

In a further exemplary aspect and as shown in FIGS. 10-14C, the means for forming at least one micropore comprises a filament array 70 that has a plurality of filaments 72 formed therein. In this aspect, each filament 72 is configured for conductively delivering thermal energy via direct contact to the tissue biological membrane to cause the ablation of some portion of that membrane deep enough to form the micropore.

In one exemplary aspect, the filament array 70 is mounted to a portion of the upper substrate surface 42. Optionally, an adhesive layer 73 can be mounted to a portion of the upper substrate surface and is configured to allow for the mounting of the electrically isolated portions of the filament array, i.e., the adhesive layer 73 is interposed between the upper substrate surface and portions of the electrically isolated portions of the filament array. In this aspect, it is contemplated that the adhesive layer 73 defines a pair of openings that are configured to allow the passage of the anode 31 and cathode 32 when the substrate is connected to the applicator. In operation, the adhesive layer 73, is connected to a portion of the bottom surface of the respective electrically isolated portions of the filament array and the portion of the upper substrate surface. This connection is configured to minimize possible vacuum loss through the ports 45 in the substrate that extend from the lower substrate surface (which are described in more detail below) when vacuum is supplied to the substrate.

In another aspect, the substrate 40 can further comprise a backing 74 that is configured to mount to and overlie at least a portion of the top surface 71 of the filament array such that a portion of the filament array in the poration area 46 is exposed. In this aspect, the filaments 72 are exposed such that they can be brought into intimate contact with body tissue. In another aspect, the backing 74 can act to electrically isolate portions of the filament array. In a further aspect, the substrate can comprise an adhesive layer 76 that is disposed between the backing and the filament array.

In another exemplary aspect, the filament array is substantially enclosed in the substrate. One would appreciate however that in this aspect, the portion of the filament array in the poration area is exposed. As noted above, the filaments are exposed such that they can be brought into intimate contact with body tissue.

In a further aspect, the filament array 70 can be, for example and not meant to be limiting, a bi-clad foil 80 comprising a conductive layer 82 and a resistive layer 84. In one aspect, the materials that the bi-clad foil is formed from can comprise, for example but not limited to: conductive material such as aluminum, copper, silver, gold, carbon, bronze, false bronze, or the like, and resistive material such as titanium, titanium nitride, tantalum, tantalum nitride, chromium, a carbon compound, tungsten, manganese, nichrom, nickel, platinum, evanohm, polysilicon, stainless steel, or the like. In one exemplary aspect, the bi-clad foil 80 comprises a conductive layer of copper and an underlying resistive layer of stainless steel.

In one exemplary aspect, the filament array 70 can be formed by a photochemical wet etching process in which an etch resist, for example and not meant to be limiting, a positive or negative acting liquid, dryfilm or powder resist, is selectively applied to the bi-clad foil via conventional methods, such as, for example, liquid coating, lamination, electrodeposition, and the like. The resist-coated foil is then exposed to UV light through a negative or positive photo-tool, creating the desired pattern. Exposed areas are cross-linked and etch-resistant, whereas non-exposed areas can be removed to expose the foil for etching.

In one example, the etching is a two-step process. In the first step, for an exemplary stainless steel/copper bi-clad foil, both metals of the bi-clad foil are etched simultaneously. In this aspect, all features on the stainless steel side of the bi-clad foil are etched to specification and features on the copper side are etched partially. The second etching step etches the conductive copper traces to specification and substantially removes all of the copper residues from the backside of the filaments. At the completion of the second etching step, the filaments are formed substantially of the stainless steel material, which are highly resistant. In one aspect, the etching process results in the removal of all of the material from between the filaments, and can optionally produce some undercutting of the relatively wide feeder traces.

Optionally, an optical machining station, or other suitable micromachining techniques such as diamond milling, electron beam etching, or the like, selectively removes portions of the conductive layers and resistive layer of the bi-clad foil to create a pattern of feeder traces and filaments. The use of a laser may be advantageous in some applications as it only requires one step and can be designed to form the pro-grammed patterns rapidly in the resistive layer, as this layer is typically thinner than the conductive layer, and/or more photo-absorbent. Optionally, an adhesive film can be applied to any layer, and a laser machining station used to remove material to form a mask for etching. In another aspect, an adhesive film can be applied to the bi-clad foil and a laser machining station is used to remove material to form a mask for etching the desired pattern in the bi-clad foil below the exposed portions of the mask.

In a further aspect, and without limitation, the bi-clad foil 80 can be produced by a cold-rolling, low-pressure process, by reduction-cold rolling, by reduction-hot rolling, explosion-bonding, plating, and the like. The bi-clad foil can be between about 10 μm to about 300 μm in a thickness (t) dimension, including additional nominal thicknesses of 20, 30, 40, 50, 60, 70, 80, 90, 100, 110, 120, 130, 140, 150, 160, 170, 180, 190, 200, 210, 220, 230, 240, 250, 260, 270, 280, and 290 μm, with 105 μm being one preferred thickness. In one aspect, it is contemplated that the filaments are substantially uniform. Optionally, the filaments can be non-uniform. Further, it is contemplated that the filaments have a substantially similar thermal mass. In one exemplary aspect, the width (w) of each filament 72, transverse to the longitudinal axis of the filament, can range between about 30 to 150 μm, including additional nominal widths of 35, 40, 35, 50, 55, 65, 70, 75, 80, 85, 90, 95, 100, 105, 110, 115, 120, 125, 130, 135, 140, and 145 μm, with a range of between about 45 and 55 µm or between 115 and 125 µm being preferred. Similarly, in another exemplary aspect, each filament 74 has a length (l) extending along the longitudinal axis of the filament, of between about 200 to 700 µm, with additional lengths of 250, 300, 350, 400, 450, 500, 550, 600, and 650 µm, with 500 µm being preferred.

Optionally, the layer of stainless steel can comprise between about 5 to about 25 percent of the thickness of the bi-clad foil, including additional amounts as 6%, 7%, 8%, 9%, 10%, 11%, 12%, 13%, 14%, 15%, 16%, 17%, 18%, 19%, 20%, 21%, 22%, 23%, and 24%, and including any range of thickness percentages derived from these values.

Figure 14C:
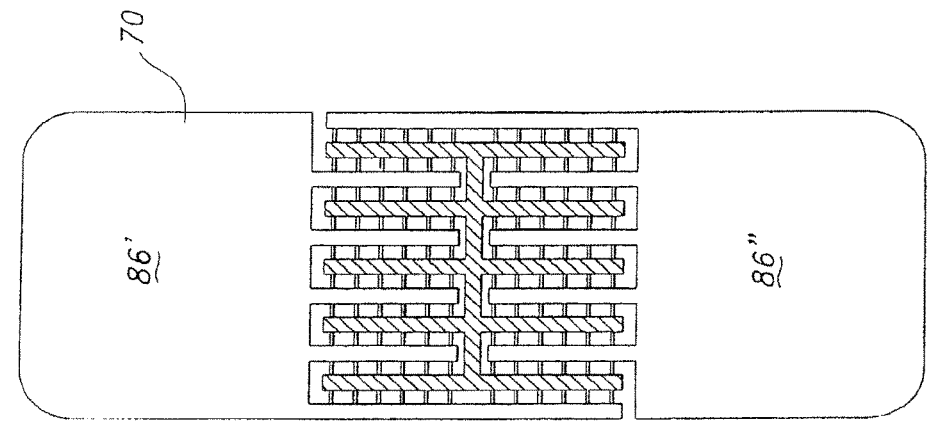
FIGS. 14A-C are schematic views of exemplary balanced filament arrays.
Figure 14B:
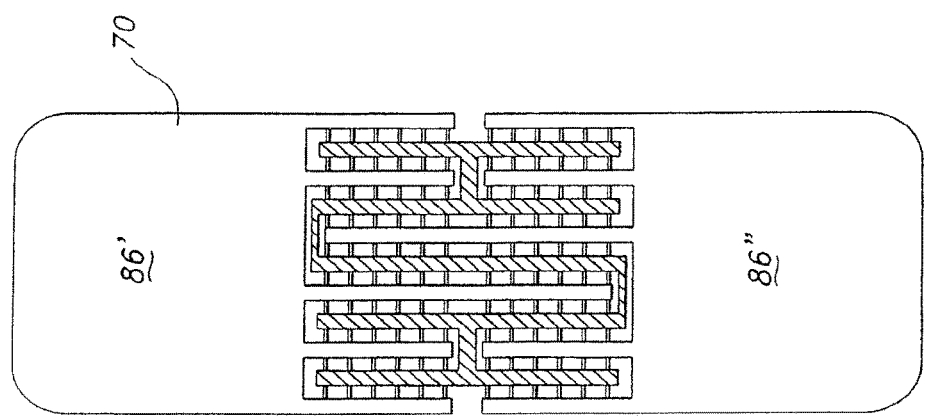
Figure 14A:
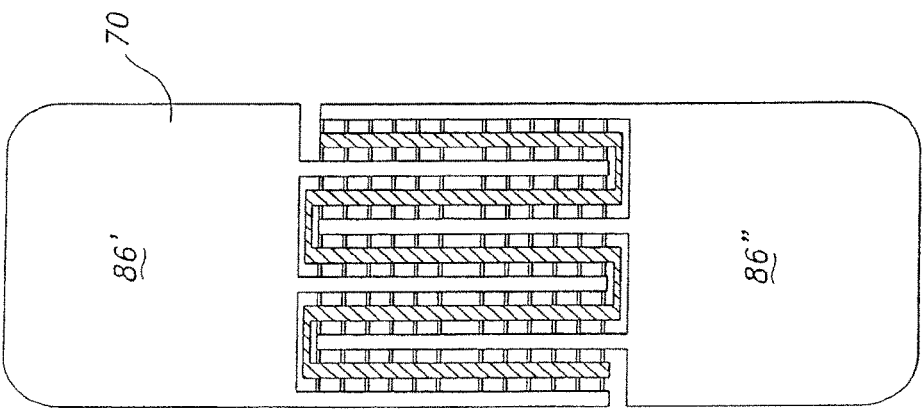

In a further aspect and referring to FIGS. 14A-14C, the filament array 70 comprises means for distributing energy to the filaments of the filament array. In one exemplary aspect, the means for distributing energy to the filaments comprises at least one electrical bank 86. Optionally, the at least one electrical bank comprises a plurality of electrical banks 86', 86''. In this aspect, each electrical bank has associated filaments 72. In one aspect of the means for distributing energy, the poration area 46 has a first portion and an opposite and/or mirrored second portion in which portions of each respective electrical bank are positioned in both the first and second portions of the poration area. In this example, the banks are geometrically shaped so that filaments of one bank are present in both "halves" or portions of the active poration area. It will be appreciated that alternative geometrically shaped banks 86 can be used such that the respective banks are distributed between respective portions of the active poration area. One skilled in the art will note that the use of such electrical banks makes the filament array 70 less sensitive to small differences in the individual filament composition and dimensions In another aspect, the substrate 40 defines a pair of ports 45 in the lower substrate surface 44 that expose respective electrically isolated portions of the filament array. In one aspect, the ports 45 are configured to accept the anode 31 and cathode 32 of the applicator 20 when the substrate is mounted to the interface 30 of the applicator such that the anode and cathode are in contact with the respective electrically isolated portion of the filament array. Thus, the filament array 70 can be placed in electrical communication with the applicator 20 when the substrate 40 is received onto the interface 30 so that electrical energy can be passed from the applicator, via the anode and cathode and the respective banks 86, to each of the filaments 72 of the filament array 70.

Figure 15:
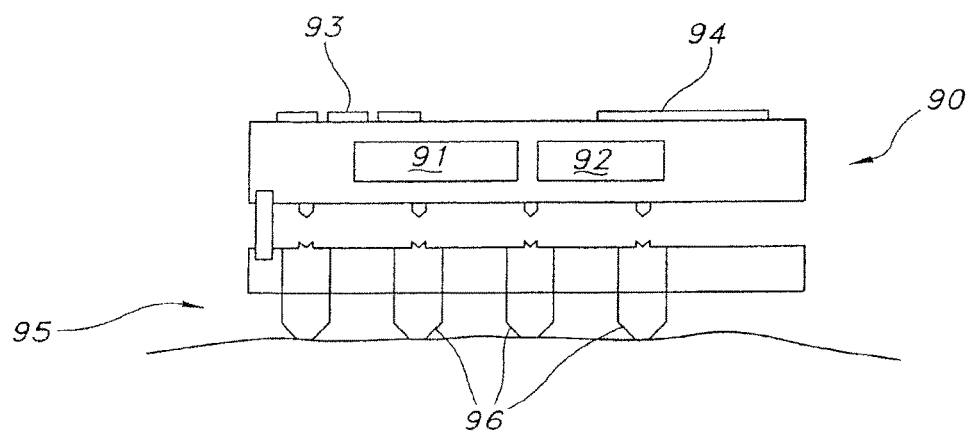
FIG. 15 is a schematic, partly sectional view of an exemplary means for forming micropores in a tissue membrane.
Figure 16:
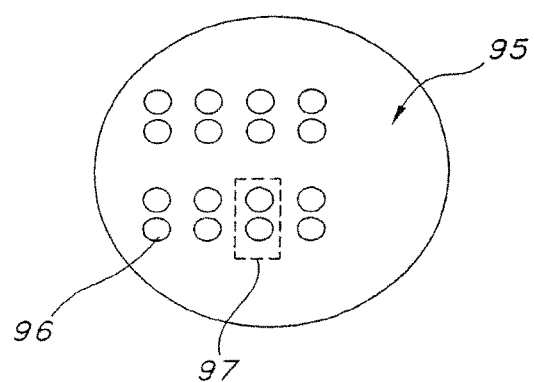
FIG. 16 is a schematic view of an electrode assembly of the means for forming micropores in a tissue membrane of FIG. 15.

In a further exemplary aspect and as shown in FIGS. 15 and 16, the means for forming at least one micropore comprises a plurality of paired electrodes. In this aspect, each pair of electrodes are configured for delivering electrical energy via direct contact to the tissue biological membrane to cause the electrical ablation of some portion of that membrane deep enough to form the micropore. For example, U.S. Pat. Nos. 5,885,211, 6,148,232, 6,615,079, and 6,711,435, the disclosures of which are incorporated herein by reference in their entirety, describe methods and devices for applying electrical energy between two or more of a plurality of electrodes, which are applied to a subject's skin, in order to cause ablation of the tissue in an area between the respective electrodes.

In one exemplary aspect, the means for forming at least one micropore further comprises a control unit 90 that is attachable to the plurality of electrodes, which is preferably fixed to a suitable area of a subject's skin. The means for forming at least one micropore can administer an active substance through the normally substantially-impermeable stratum corneum layer of the skin by passing a controlled electric current between the plurality of electrodes, which ablates the stratum corneum and generates micro-channels through which the substance can pass.

In one aspect, when means for forming at least one micropore drives current through the stratum corneum, the affected tissue is heated resistively, so that the tissue is ablated by the total energy dissipated therein when a sufficient quantity of energy has passed therethrough in a short time period. The ablation creates the desired micropores in the form of micro-channels in the tissue. In an additional aspect, the application of a current to a small area of the skin leads to formation of micro-channels that can be sized to allow for even large molecules to pass relatively freely, without the necessity of ionizing or polarizing the molecules, and without causing pain or substantial trauma to the dermis and epidermal tissue underlying the stratum corneum.

In one aspect, the control unit 90 comprises a switching unit 91, a battery 92 (such as a lithium coin cell battery), and an optional user-interface comprising buttons 93 and a sensible signal generator 94, which may comprise a display and/or a buzzer. In one exemplified aspect, the buttons 93 initialize and terminate delivery of the active substance.

FIG. 16 shows an array 95 of electrodes 96 that comprises sixteen electrodes. It is of course contemplated that the array might be smaller, while in others the array might be larger, for example 50×50 or even more, so as to enable a greater amount of the active substance to be delivered. In the illustrated aspect, the electrodes 96 in this embodiment are preferably organized into eight electrode pairs 97, such that most of the charge leaving one electrode in a pair goes to the other electrode in that respective pair and generally does not go to electrodes in an adjacent pair of electrodes. In one aspect, electrode pairs 97 can be densely packed in order to maximize the transdermal transfer rate. For example and not meant to be limiting, the density may range from 4-100 electrode sets/cm$^2$. In a further aspect, each electrode pair typically generates at least one micro-channel before a threshold of current or total charge transfer is passed, in response to which, the switching unit 91 causes current to the electrode pair to be terminated or reduced.

Preferably, the spacing between electrodes in each electrode pair is smaller than about 0.1 mm, although, for example and not meant to be limiting, it may range from between about 0.1 min to about 0.3 mm. Generally, the distance between the respective electrodes of an electrode pair is set such that a desired electric field penetration depth is achieved. In one example, the desired electric field penetration depth is substantially of the same magnitude as the thickness of the stratum corneum, so that the current mostly does not enter epidermal tissue underlying the stratum corneum. In this exemplary aspect, maintaining the electrode spacing between about 0.01 mm and about 0.1 mm, including additional spacing of 0.02, 0.03, 0.04, 0.05, 0.06, 0.07, 0.08, and 0.09 mm, generates micro-channels therein the stratum corneum while substantially reducing damage, sensation and/or pain in the innervated dermis and in the epidermal tissue below the stratum corneum.

At any point in the skin in a vicinity of two electrodes placed thereon, the electric field generated between the electrodes can be viewed as having fundamentally two components: a component perpendicular to the skin, which generally causes current flow perpendicular to the skin; and a lateral component, which generally causes current flow parallel to the skin surface. An electric field at the base of the stratum corneum having a relatively large lateral component generates current flow predominantly in the stratum corneum, with relatively little current flow into the underlying epidermal tissue. Thus, in one aspect, tissue ablation can be restricted to occur mostly in the stratum corneum However, it is contemplated that the means for forming at least one micropore can be used to form micropores, i.e., microchannels in this example, that extend to a desired penetration depth below the stratum corneum layer.

In a further aspect, the electrode array is disconnected from the switching unit or power source at substantially the same time as ablation of the stratum corneum is completed. In one aspect, the switching unit 91 can monitor current flow to the electrodes 96 and selectively terminates the flow to one or more electrodes upon a determination that ablation of the underling tissue has occurred. In this exemplary aspect, the current flow to all of the electrodes in the array is substantially terminated upon a determination by the switching unit 91 that the underlying tissue under the electrode array has been ablated.

In yet another aspect, the substrate 40 can define at least one female depression 140 that is defined on the lower substrate surface 44. In this aspect, the at least one of female depression is configured to cooperate with a series of depressible elements 142 mounted on the interface 30 of the applicator 20. The depressible elements are in communication with the controller board of the applicator. In one exemplary aspect, there are three depressible elements such that, in an exemplary operation, if a substrate having two female depressions is mounted to the interface, only one of the depressible elements of the applicator would be depressed. In this example, the depression of only one of the three depressible elements would electrically communicate to the controller board the respective size of the poration area of the substrate that is mounted on the interface. One would appreciate that, in this example, selective depression of the depressible elements can communicate varying sizes of the poration area of the respective substrate.

In a further aspect of the invention, the delivery system 10 further comprises a first release liner 110 that has a top surface 112 and an opposed bottom surface 114. In one aspect, at least a portion of the bottom surface of the first release liner is connected to a portion of the upper substrate surface 42. In another aspect, the system can comprise an adhesive layer 116 positioned therebetween the upper surface of the substrate 40 and the bottom surface 114 of the first release liner to connect the substrate 40 to the first release liner 110. In one aspect, an edge portion of first release liner is spaced a predetermined distance from the poration area of the substrate. Optionally, the edge portion of the first release liner is positioned substantially adjacent to a portion of the ridge formed on the upper substrate surface. In this aspect, if the substrate defines the female depression in the upper substrate surface, the adhesive layer can be positioned adjacent a portion of the ridge of the female depression and the edge portion of the first release liner can also be positioned adjacent the portion of the ridge. In a further aspect, the patch 100 is selectively removable from the top surface 112 of the first release liner.

In a further aspect, the patch 100 can comprise a backing layer 102 and a reservoir 104 mounted to a portion of the backing layer. The reservoir 104 is configured for releaseably containing the at least one permeant for delivery into the tissue membrane of the subject via the formed micropores. In one aspect, the reservoir 104 is mounted on a portion of a lower surface 106 of the backing layer 102. As shown in the figures, in a connected position, a first portion 107 of the backing layer 102 is releaseably mounted to the top surface 112 of the first release liner in spaced registration with the poration area 76 of the substrate 40. Further, in the connected position, a second portion 108 of the backing layer 102 is folded back into a folded position. As one skilled in the art will appreciate, the lower surface 106 of the second portion 108 of the backing layer faces outwardly away from the upper substrate surface 42 of the substrate in the folded position.

In a further aspect, the patch 100 can comprise a skin adhesive layer 103 disposed on at least a portion of the lower surface 106 of the backing layer of the patch such that the patch can be selectively releasably mounted to the tissue membrane of the subject. In another aspect, the delivery system 10 can further comprise a second release liner 120 that is releaseably mountable to a portion of the skin adhesive layer 103 that is disposed thereon the second portion of the backing layer. Optionally, an adhesive anchor layer 105, such as, for example, double-sided adhesive and the like, can be mounted onto a portion of the filament array backing layer 74. In this aspect, the second release liner can be releaseably mounted to a portion of the skin adhesive layer 103 and the adhesive anchor layer.

The second release liner 120 provides a releasable cover that protects the otherwise exposed portion of the skin adhesive layer during storage. In this aspect, it is contemplated that the force required to remove the second release liner 120 from the skin adhesive layer 103 would be less than the force required to remove the first portion 107 of the backing layer 102 from the top surface of the first release liner. Thus, the second release liner 120 can be removed from the patch 100 to expose the folded over portion of the skin adhesive layer 103 without separating the patch 100 from the top surface 112 of the first release liner 110. In one aspect, a slit 122 can be defined therein a portion of the second release liner 120 so that the second release liner can be readily grasped and removed without imparting undo force to the underlying structure, i.e., without separating the patch 100 from the top surface 112 of the first release liner 110.

In a further aspect, the top surface 112 of the first release liner can have a release coating disposed thereon. The release coating can be any conventional release coating comprising, for example and not meant to be limiting, silicone, platinum-catalyzed silicone, fluorosilicone, perfluorocarbon-based polymer, and the like.

In the connected position, in another aspect, the first portion 107 of the backing layer 102 is positioned in folded registration with the poration area 76 of the substrate 40. As exemplified in the figures, the fold can be spaced a predetermined distance from the poration area. In one aspect, an edge of the reservoir 104 can be spaced substantially adjacent to the fold. Optionally, the reservoir can be spaced a predetermined distance from the fold. In the exemplified aspects, the reservoir is positioned in registration with the fold.

Figure 4:
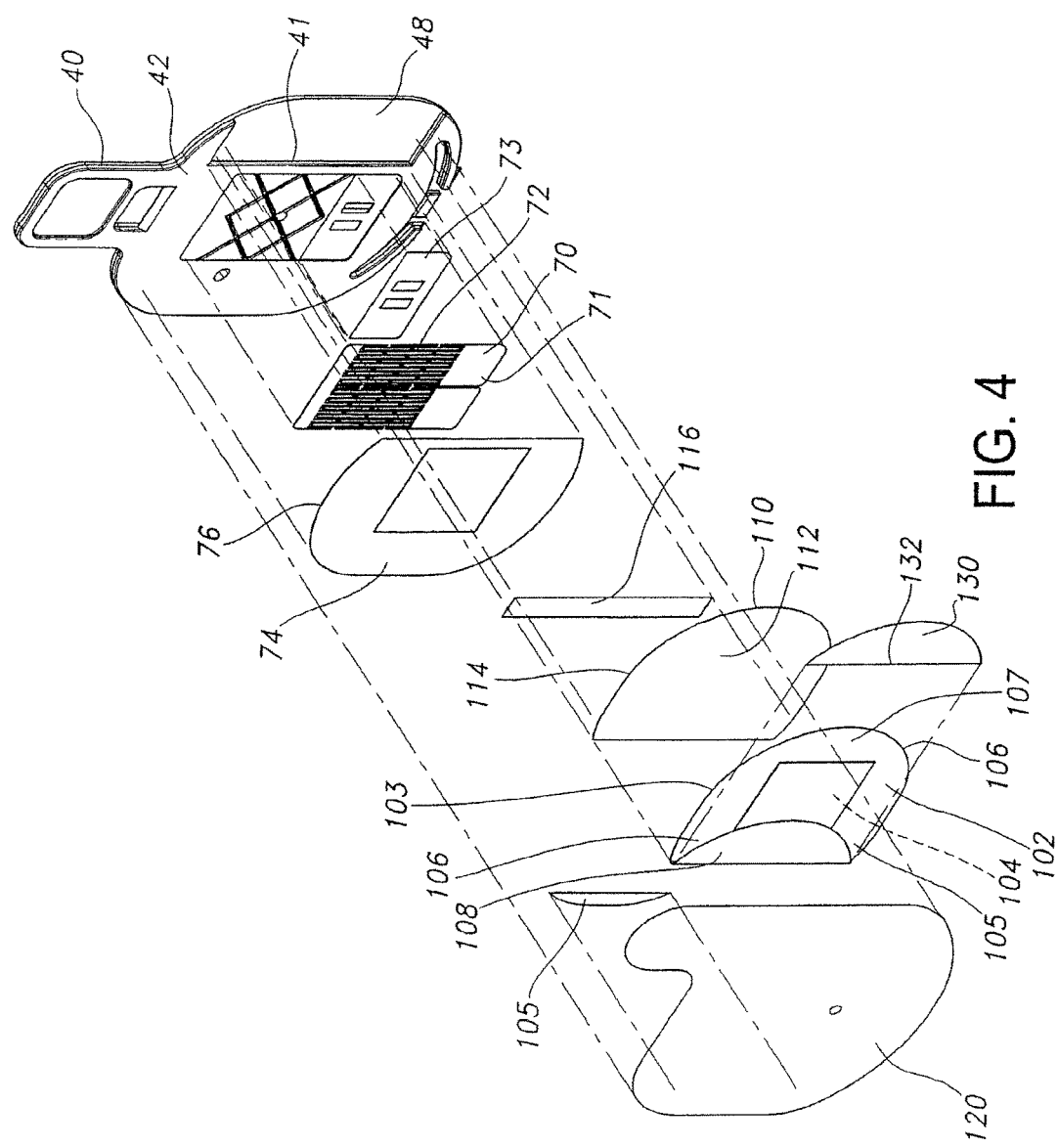
FIG. 4 is an exploded view of the first embodiment of the transdermal patch of FIG. 1.
Figure 5:
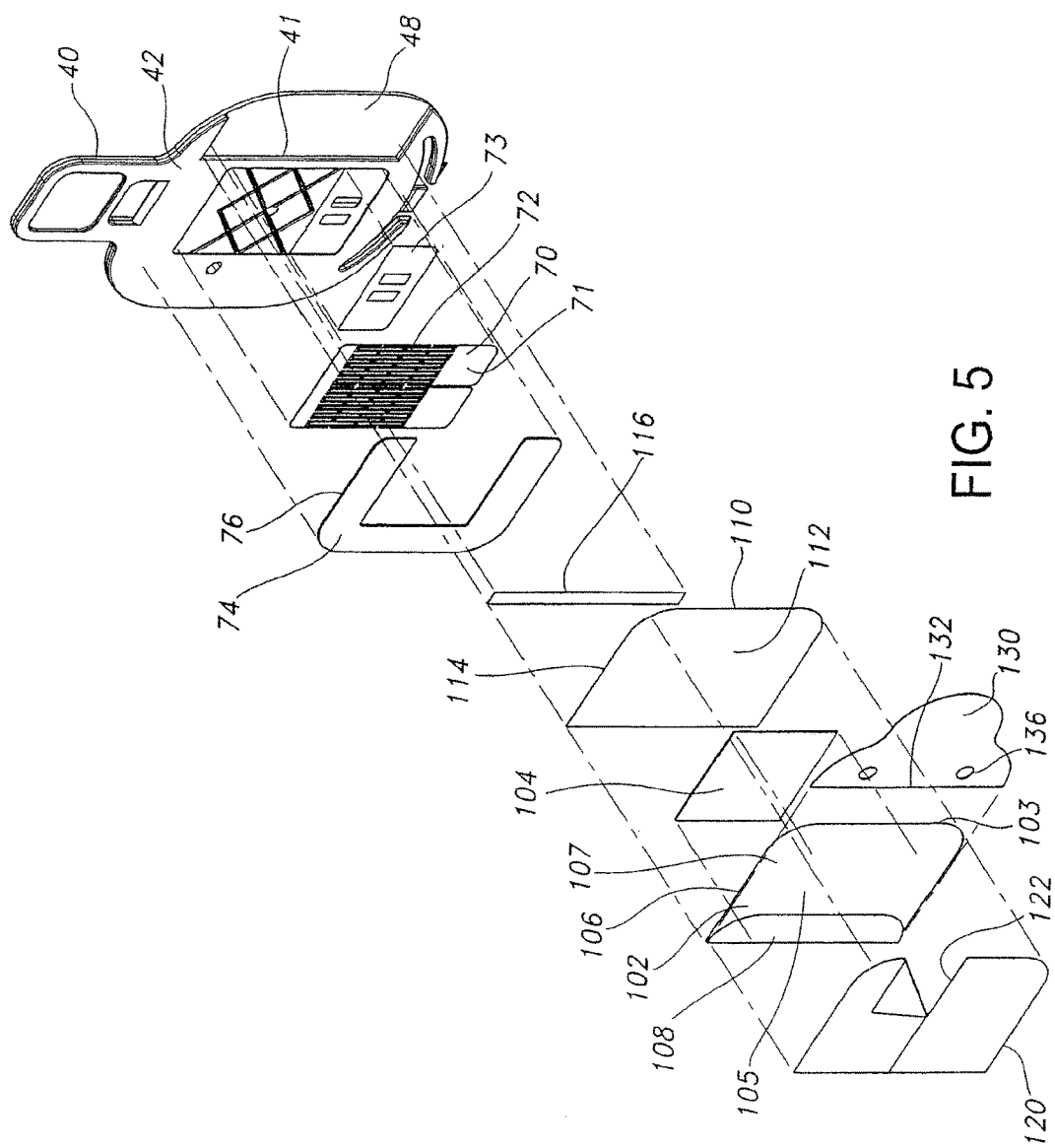
FIG. 5 is an exploded view of a second embodiment of the transdermal patch of the present invention.
Figure 6:
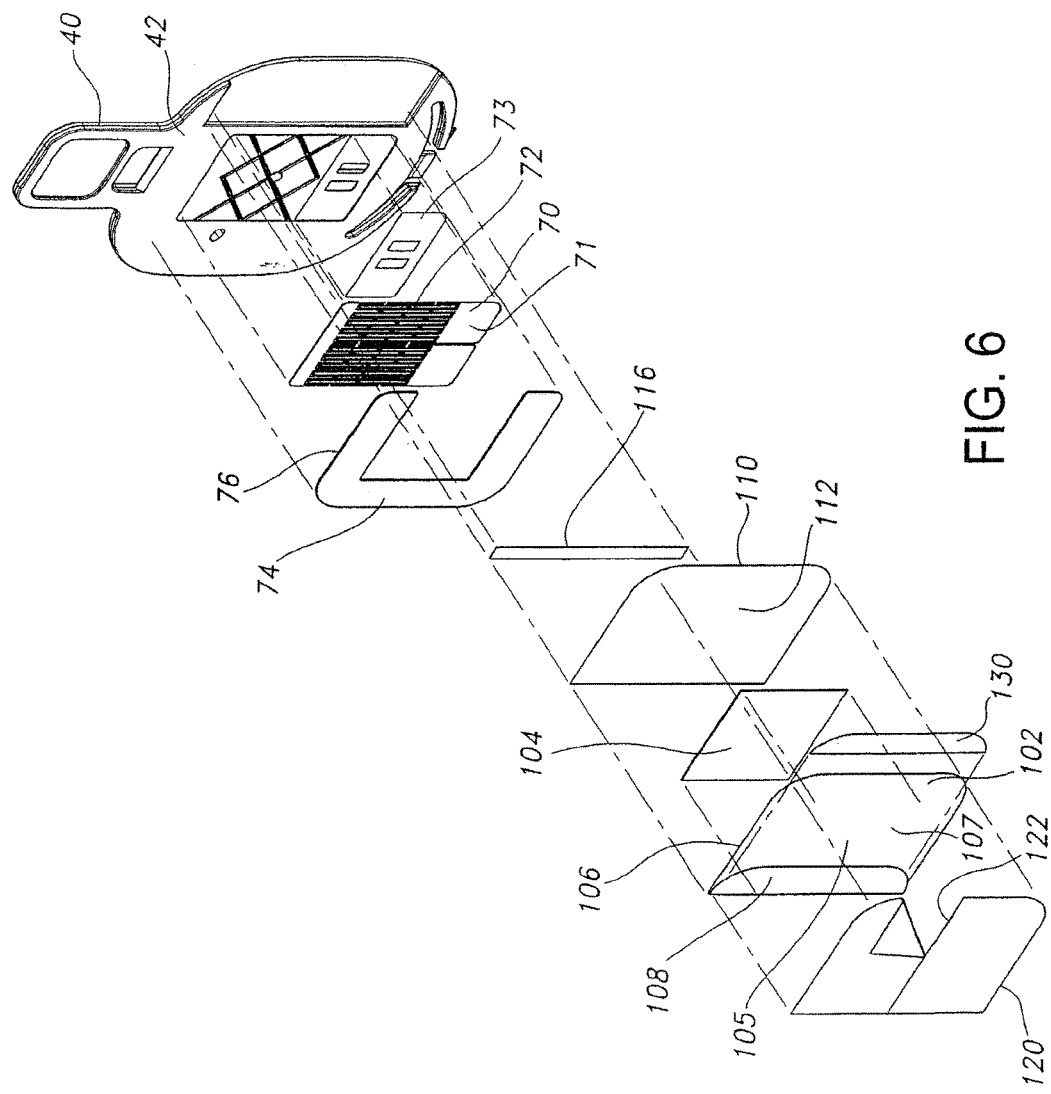
FIG. 6 is an exploded view of a third embodiment of the transdermal patch of the present invention.
Figure 7:
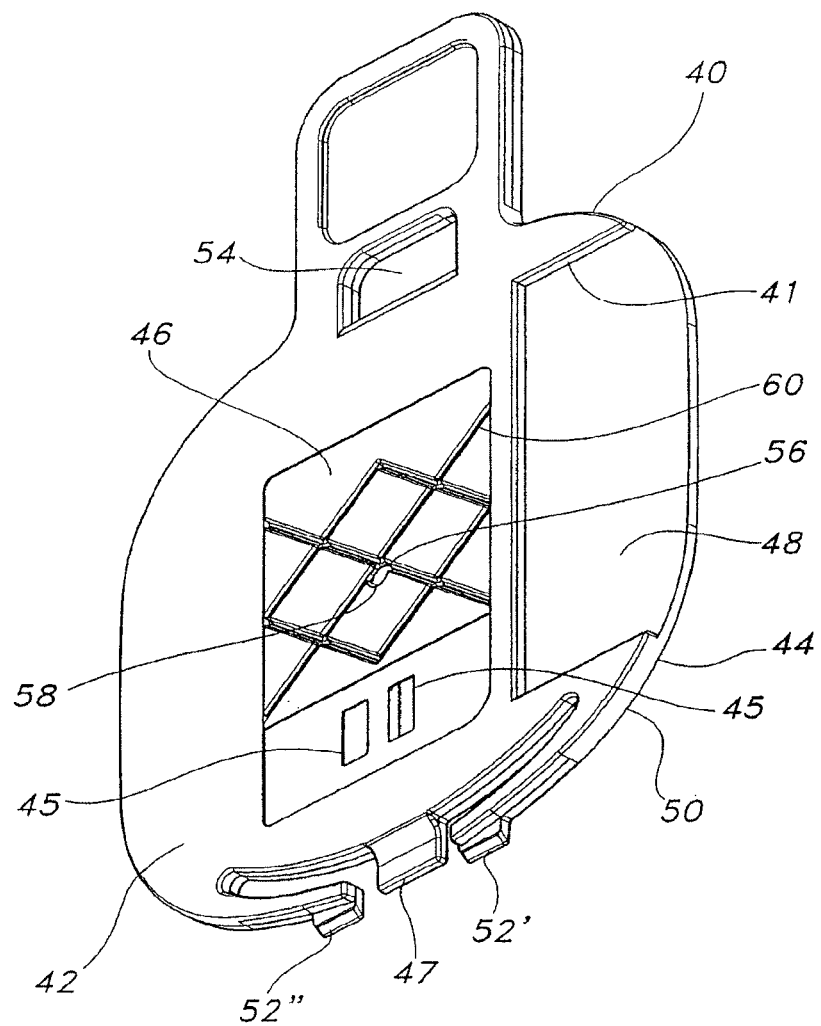
FIG. 7 is an exploded view of an embodiment of the substrate of the transdermal delivery system, showing a ridge extending outwardly from the upper substrate surface.
Figure 8:
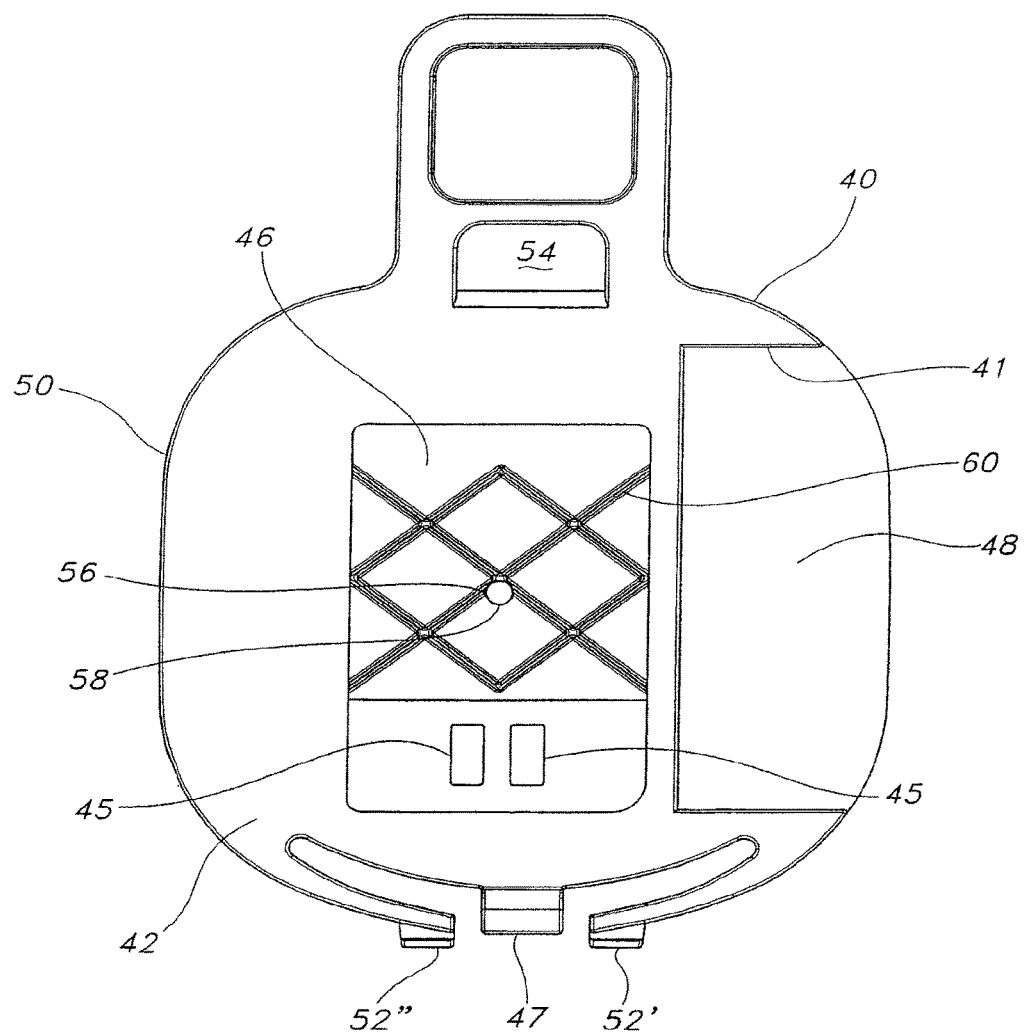
FIG. 8 is a top elevational view of the substrate of FIG. 7.
Figure 9:
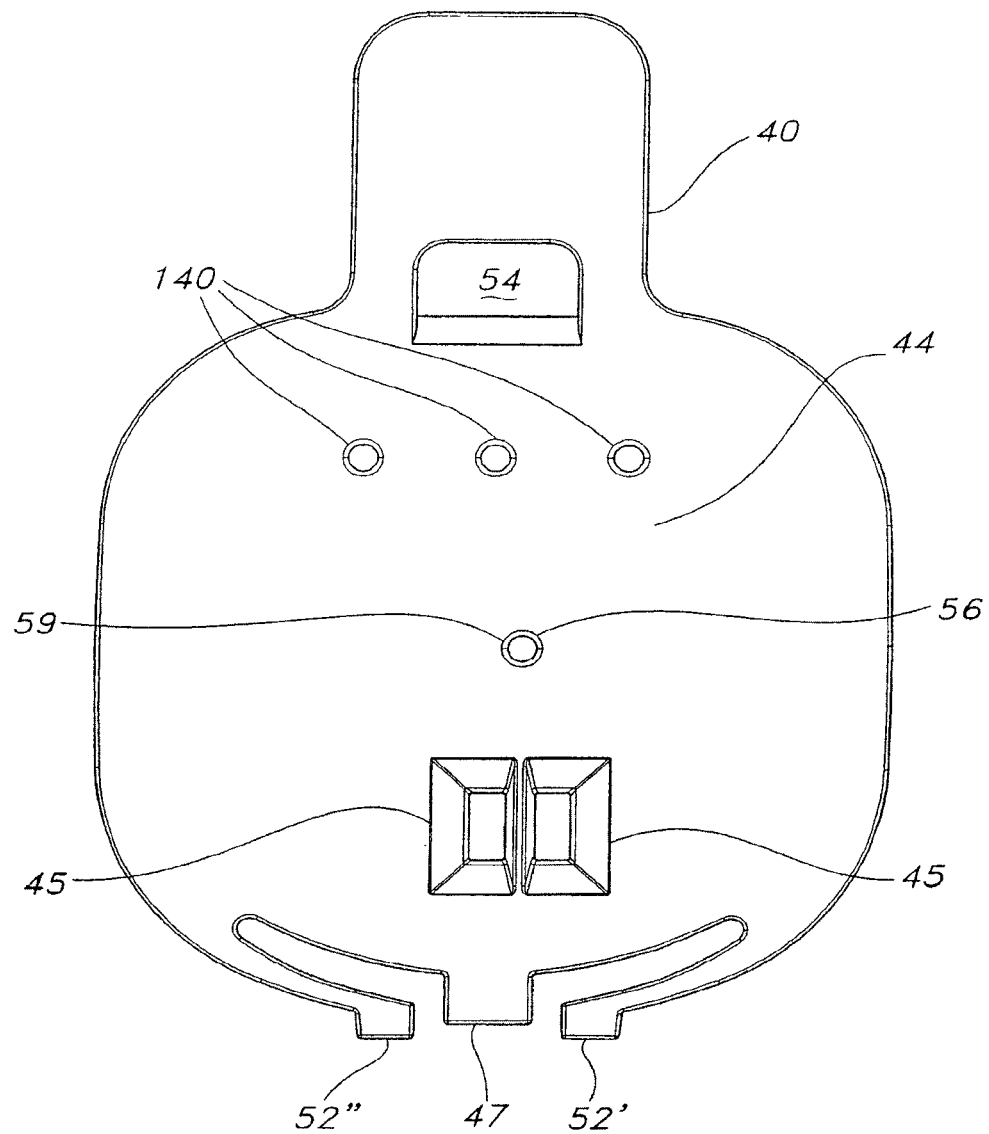
FIG. 9 is a bottom elevational view of the substrate of FIG. 8.
Figure 10:
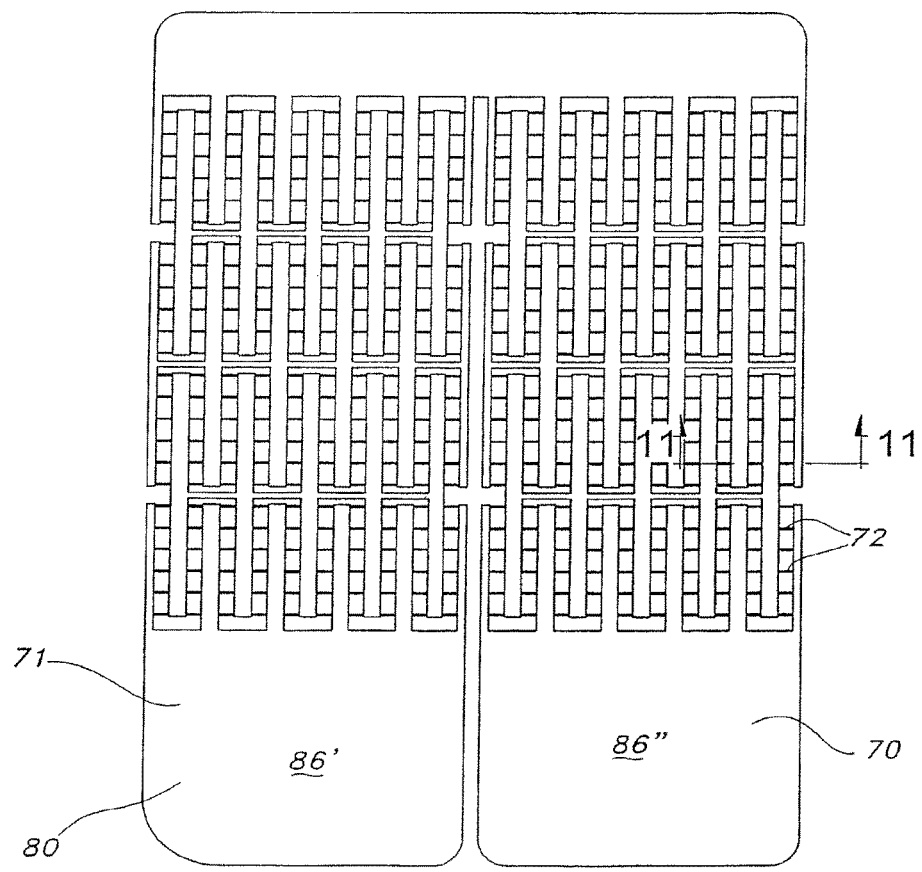
FIG. 10 is a top elevational view of one embodiment of a filament array.
Figure 11:
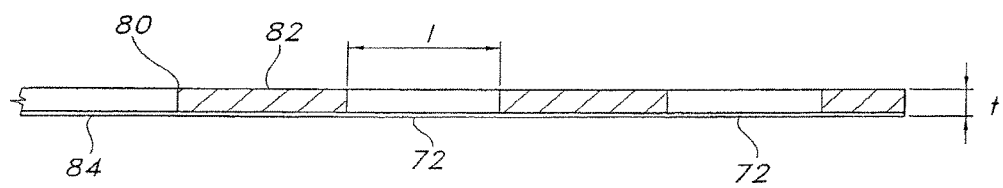
FIG. 11 is an enlarged cross sectional view of the filament array taken across line 11 of FIG. 10.
Figure 12:
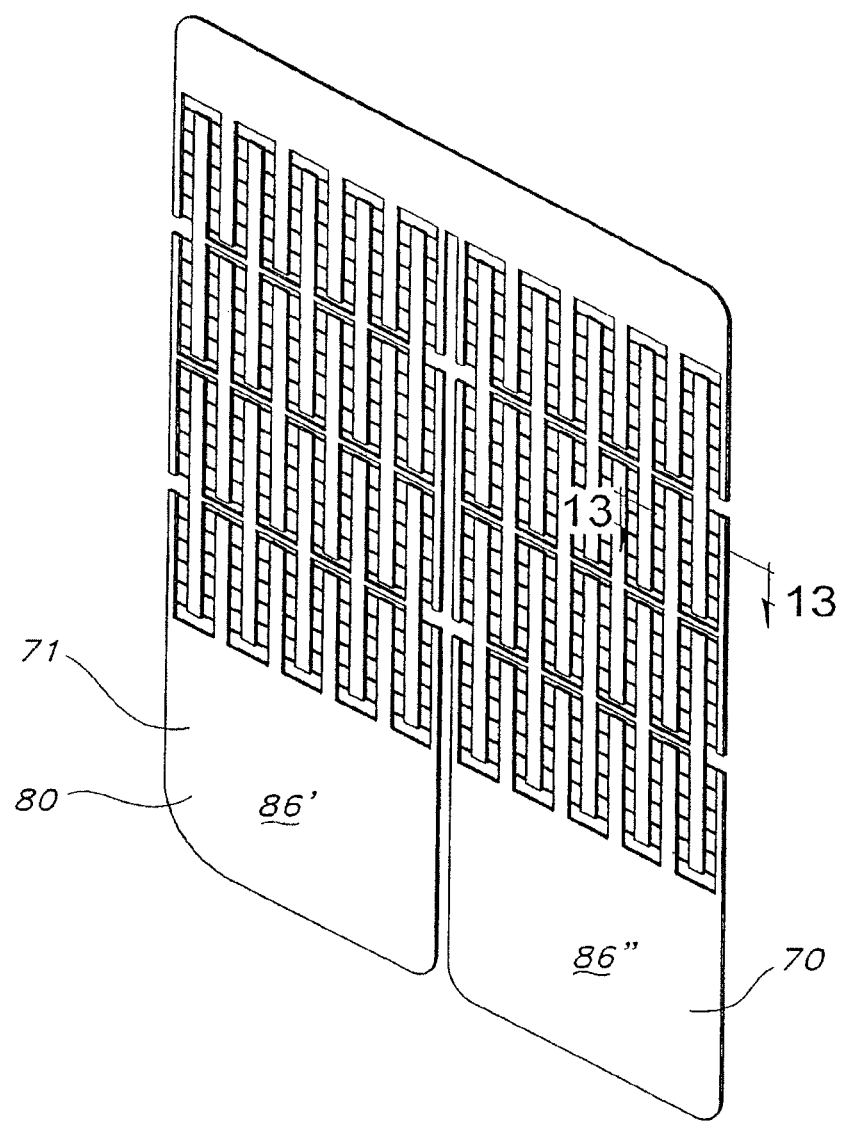
FIG. 12 is a perspective view of the filament array of FIG. 10.
Figure 13:
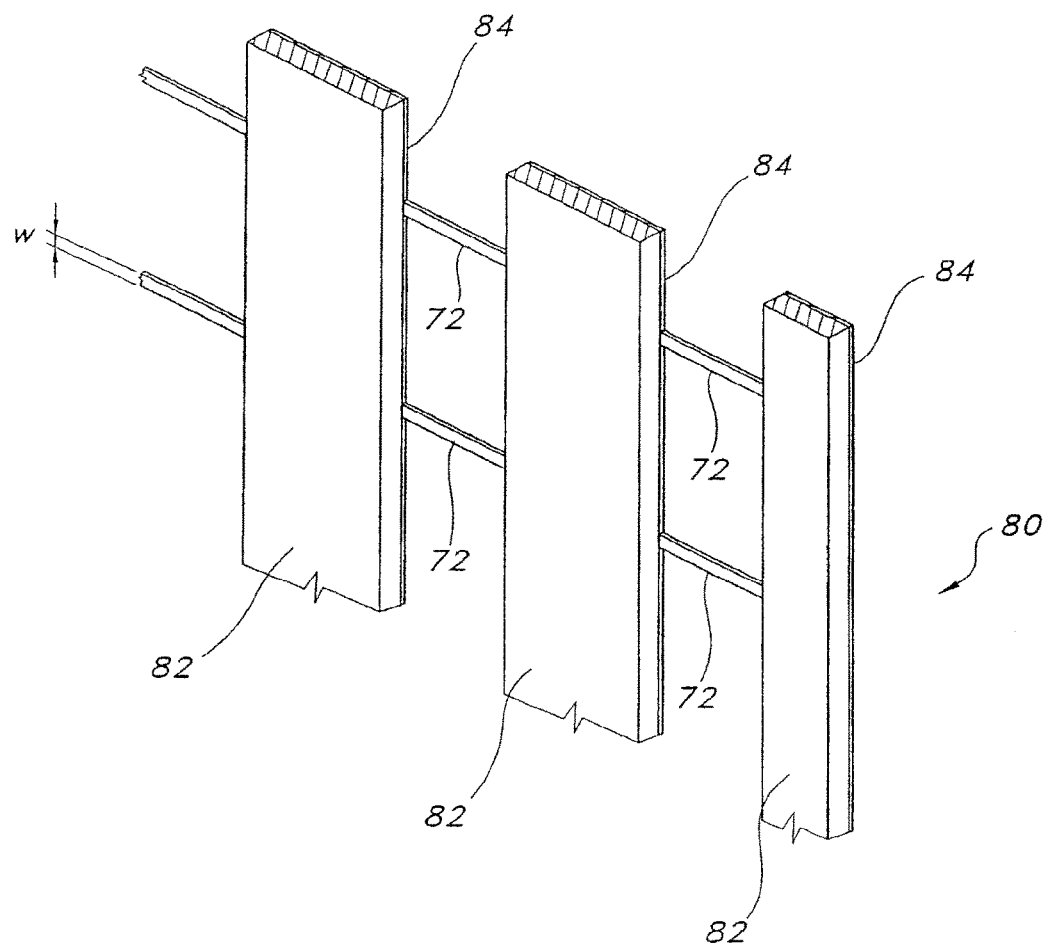
FIG. 13 is a cross-sectional view of the filament taken across line 13 of FIG. 12.

Referring now to FIGS. 4-6, a portion of the first portion 107 of the backing layer 102 underlies the second portion 108 of the backing layer in the connected position. In a further aspect, the system 10 can comprise a support member 130 that is positioned on portions of the upper surface 105 of the backing layer 102. In one aspect, the support member 130 has an edge surface 132. Further, in yet another aspect, the support member 130 can be releaseably mounted onto portions of the upper surface 105 of the backing layer such that, in the connected position, the support member 130 is positioned between the upper surface 105 of the second portion 108 of the backing layer 102 and a portion of the upper surface 105 of the first portion 107 of the backing layer 102.

In one exemplified aspect, the edge surface 132 of the support member 130 is positioned adjacent to the fold. In another aspect, the support member can comprise a substantially planar member. In this aspect, the support member can also comprise a portion that is folded back onto itself to form the edge surface. Optionally, the portion that is folded back onto itself can be secured into position with an adhesive.

In yet another exemplary aspect, the support member 130 can define at least one hole 136 that extends therethough the support member. In this aspect, the support member can be selectively secured relative to the backing layer by heat welding overlapping portions of the backing layer that are in registration with the at least one hole. In operation, when the patch is folded over onto the microporated tissue membrane, the heat welded "tacks" would break apart to allow for the registration of the reservoir of the patch with the microporated portion of the tissue membrane.

In a further exemplary aspect, the support member can define a pair of opposed tabs that are configured to extend beyond the outer edge of the backing layer. In one aspect, the tabs are secured to the upper substrate surface by the use of tape or the like that overlies the respective tabs and is secured to portions of the upper substrate surface. In one aspect, the portion of the tape that overlies the respective tabs can be non-adhesive such that the respective tabs are not adhesively connected to the overlying tape.

In another exemplary aspect, the support member 130 can further comprise an adhesive tape 134 that is mounted therebetween a portion of the overlapping first and second portions of the backing layer 102. In this example, the tape can be positioned between the upper surface 105 of the second portion 108 of the backing layer and a portion of the upper surface 105 of the first portion 107 of the backing layer in the connected position. In operation, when the patch 100 is folded over onto the microporated portion of the tissue membrane, the adhesive tape 134 is configured to release from the backing layer 102.

Figure 20:
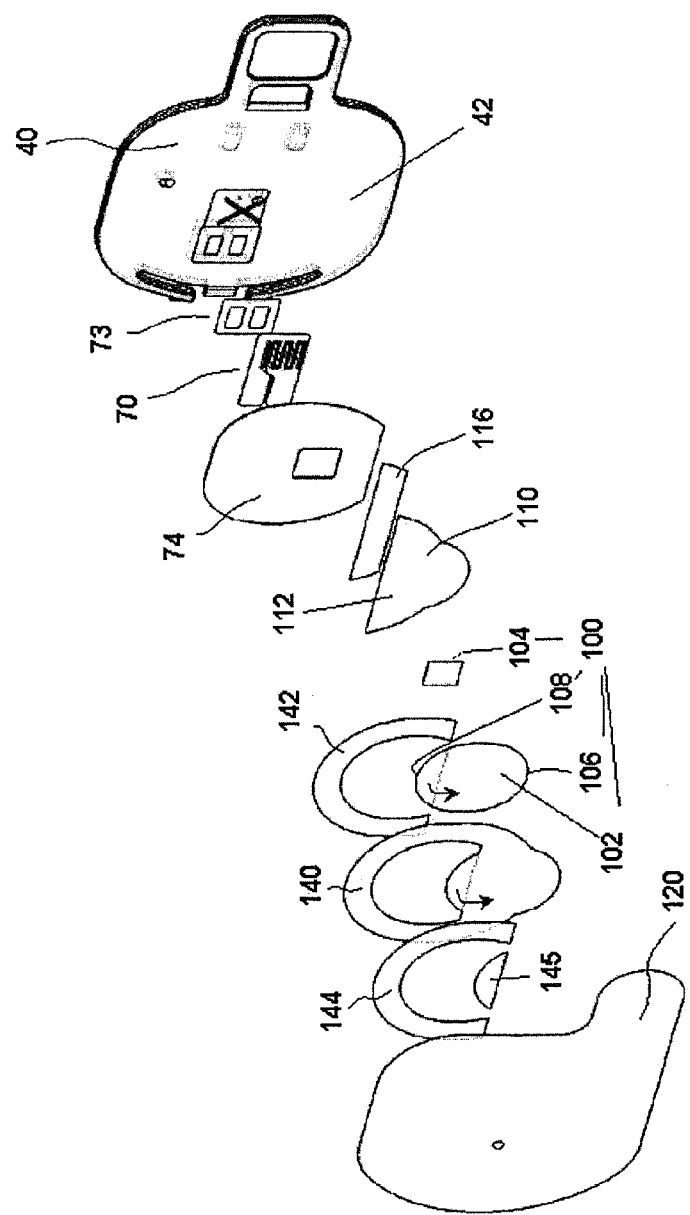
FIG. 20 is an exploded view of a fourth embodiment of the transdermal patch of the present invention.

Referring to FIG. 20, an alternative embodiment of the delivery system is schematically illustrated. In this aspect, the delivery system 10 further comprises a first release liner 110 that has a top surface 112 and an opposed bottom surface 114. In one aspect, at least a portion of the bottom surface of the first release liner is connected to a portion of the backing 74. In another aspect, the system can comprise an adhesive layer 116 positioned therebetween the upper surface of the backing and the bottom surface 114 of the first release liner to connect the backing 74 to the first release liner 110. In one aspect, an edge portion of first release liner is spaced a predetermined distance from the poration area of the substrate. In a further aspect, the patch 100 is selectively removable from the top surface 112 of the first release liner.

In a further aspect, the patch 100 can comprise a backing layer 102 and a reservoir 104 mounted to a portion of the backing layer. The reservoir 104 is configured for releaseably containing the at least one permeant for delivery into the tissue membrane of the subject via the formed micropores. In one aspect, the reservoir 104 is mounted on a portion of a lower surface 106 of the backing layer 102. As shown in the figures, in a connected position, a first portion 107 of the backing layer 102 is releaseably mounted to the top surface 112 of the first release liner in spaced registration with the poration area of the substrate 40. Further, in the connected position, a second portion 108 of the backing layer 102 is folded back into a folded position. As one skilled in the art will appreciate, the lower surface 106 of the second portion 108 of the backing layer faces outwardly away from the upper substrate surface 42 of the substrate in the folded position.

In a further aspect, the patch 100 can comprise a skin adhesive layer 103 disposed on at least a portion of the lower surface 106 of the backing layer of the patch such that the patch can be selectively releasably mounted to the tissue membrane of the subject. In a further aspect, the delivery system can further comprise a patch backing film 140 that is connected to a portion of the backing 74. In this aspect, an adhesive layer 142 can be attached to a first portion of the bottom side of the patch backing film and a portion of the backing. Further, it is contemplated that at least a portion of the upper surface of the backing 102 layer of the patch can be selectively mounted to a second portion of the bottom side of the patch backing film 140. In yet another aspect, the delivery system 10 can further comprise a second release liner 120 that is releaseably mountable to a portion of the top side of the patch backing film. Optionally, a skin adhesive layer 144, such as, for example, double-sided adhesive and the like, can be mounted therebetween the portion of the top side of the patch backing film, opposite the first portion of the bottom side of the patch backing film, and the second release liner. In another aspect, a portion of the second release liner can also be releasably connected to the second portion 108 of the backing layer of the patch 100 in the connected position. In this aspect, an adhesive layer 145 can be interposed between the folded over portion of the patch backing film.

In this aspect, it is contemplated that the force required to remove the second release liner 120 from the skin adhesive layer 144 would be less than the force required to remove the patch backing film from the top surface of the first release liner. Thus, in this aspect, the second release liner 120 can be removed from the patch 100 to expose the folded over portion of the skin adhesive layer 103 without separating the patch 100 from the top surface 112 of the first release liner 110.

In a further aspect, the top surface 112 of the first release liner can have a release coating disposed thereon. The release coating can be any conventional release coating comprising, for example and not meant to be limiting, silicone, platinum-catalyzed silicone, fluorosilicone, perfluorocarbon-based polymer, and the like.

In the connected position, in another aspect, the first portion 107 of the backing layer 102 is positioned in folded registration with the poration area 76 of the substrate 40. As exemplified in the figures, the fold can be spaced a predetermined distance from the poration area. In one aspect, an edge of the reservoir 104 can be spaced substantially adjacent to the fold. Optionally, the reservoir can be spaced a predetermined distance from the fold. In the exemplified aspects, the reservoir is positioned in registration with the fold.

Figure 21:
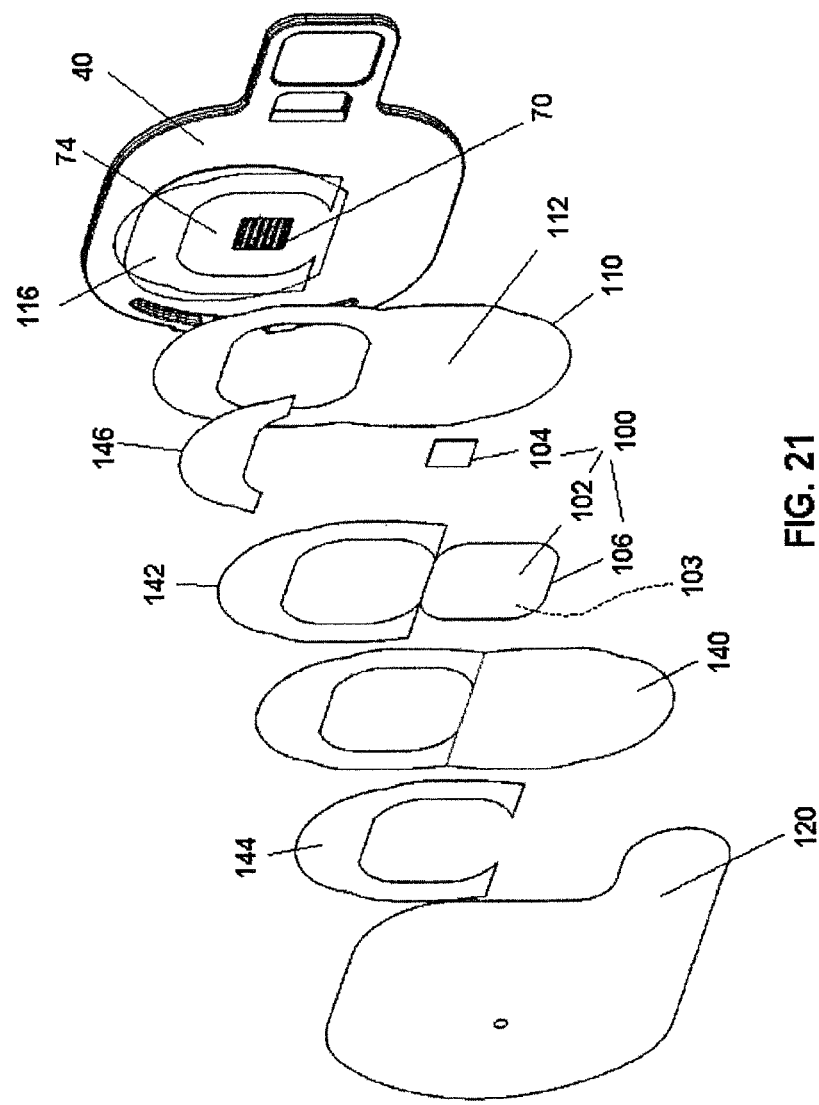
FIG. 21 is an exploded view of a fifth embodiment of the transdermal patch of the present invention.

Referring to FIG. 21, an alternative embodiment of the delivery system is partially schematically illustrated. In this aspect, the delivery system 10 further comprises a first release liner 110 that has a top surface 112 and an opposed bottom surface 114. In one aspect, at least a portion of the bottom surface of the first release liner is connected to a portion of the backing 74. In another aspect, the system can comprise an adhesive layer 116 positioned therebetween the upper surface of the backing and the bottom surface 114 of the first release liner to connect the backing 74 to the first release liner 110. In one aspect, an edge portion of first release liner is spaced a predetermined distance from the poration area of the substrate. In a further aspect, the patch 100 is selectively removable from the top surface 112 of the first release liner.

In a further aspect, the patch 100 can comprise a backing layer 102 and a reservoir 104 mounted to a portion of the backing layer. The reservoir 104 is configured for releaseably containing the at least one permeant for delivery into the tissue membrane of the subject via the formed micropores. In one aspect, the reservoir 104 is mounted on a portion of a lower surface 106 of the backing layer 102 of the patch 100. As shown in the figures, in a connected position, a portion of the backing layer 102 is releaseably mounted to the top surface 112 of the first release liner in spaced registration with the poration area of the substrate 40.

In a further aspect, the patch 100 can comprise a skin adhesive layer 103 disposed on at least a portion of the lower surface 106 of the backing layer 102 of the patch such that the patch can be selectively releasably mounted to the tissue membrane of the subject. In a further aspect, the delivery system can further comprise a patch backing film 140 that is connected to a portion of the top surface of the first release liner. In this aspect, an adhesive layer 142 can be attached to a first portion of the bottom side of the patch backing film and a portion of the top surface of the first release liner. Further, it is contemplated that a de-blocking member 146 can be mounted therebetween a portion of the bottom side of the adhesive layer and the top surface of the first release liner 110 such that it is easier to selectively separate the adhesive layer 142 from the first release liner 110. Further, it is contemplated that at least a portion of the upper surface of the backing 102 layer of the patch can be selectively mounted to a second portion of the bottom side of the patch backing film 140. In yet another aspect, the delivery system 10 can further comprise a second release liner 120 that is releaseably mountable to a portion of the top side of the patch backing film. Optionally, a skin adhesive layer 144, such as, for example, double-sided adhesive and the like, can be mounted therebetween the portion of the top side of the patch backing film, opposite the first portion of the bottom side of the patch backing film, and the second release liner.

In this exemplary embodiment, it is contemplated that the force required to remove the second release liner 120 from the skin adhesive layer 144 would be less than the force required to remove patch backing film from the top surface of the first release liner. Thus, the second release liner 120 can be removed from the patch 100 to expose the skin adhesive layer without separating the patch 100 from the top surface 112 of the first release liner 110.

In a further aspect, the top surface 112 of the first release liner can have a release coating disposed thereon. The release coating can be any conventional release coating comprising, for example and not meant to be limiting, silicone, platinum-catalyzed silicone, fluorosilicone, perfluorocarbon-based polymer, and the like.

In the connected position, in another aspect, the backing layer 102 is positioned in folded registration with the poration area 76 of the substrate 40. As exemplified in the figures, the fold can be spaced a predetermined distance from the poration area. In one aspect, an edge of the reservoir 104 can be spaced substantially adjacent to the fold. Optionally, the reservoir can be spaced a predetermined distance from the fold. In the exemplified aspects, the reservoir is positioned in registration with the fold.

In one exemplified aspect of the transdermal delivery system, the reservoir 104 comprises a designated area or chamber within the patch 100 that is configured to contain a permeant for delivery through the formed artificial opening or micropore in the tissue or biological membrane into the subject. In one aspect, it is contemplated that the reservoir can also comprise excipient compounds which enhance the effect of a bio-active permeant. Additionally, in various exemplified aspects and not meant to be limiting, the reservoir may be comprised of an open-volume space, a gel, a flat planar space which has been coated or treated with a selected compound for subsequent release or reaction, or a permeable solid structure such as a porous polymer.

In an alternative embodiment, the reservoir 104 can comprise at least one undissolved hydrophilic permeant disposed therein. When the reservoir is positioned in registration with the micropores through operation of the transdermal delivery system of the present invention, the hydrophilic permeant can come in contact with subcutaneous fluid when the bottom surface of the reservoir is in fluid communication with the at least one formed micropore or pathway through the skin layer of a subject. Once an effective amount of subcutaneous fluid has come into contact with the delivery reservoir, the fluid subsequently provides a diffusion path for transdermally delivering at least a portion of the permeant contained in the reservoir through the skin and into the subject.

The reservoir 104 of this aspect can comprise a non-biodegradable matrix which, as stated above, further comprises at least one hydrophilic permeant disposed therein. The matrix component of the permeant delivery reservoir is comprised of a non-biodegradable material or combination of non-biodegradable materials that are biocompatible for topical application to the outer skin layer of a subject for extended permeant application periods. The non-biodegradable material can, in one aspect, account for approximately 20 weight % to approximately 80 weight % of the reservoir, including additional amounts as 25 weight %, 30 weight %, 35 weight %, 40 weight %, 45 weight %, 50 weight %, 55 weight %, 60 weight %, 65 weight %, 70 weight %, and 75 weight % of the reservoir, and including any range of weight percentages derived from these values.

In one aspect, the non-biodegradable matrix can comprise a non-biodegradable polymeric material or combination of polymeric materials. In one aspect, the non-biodegradable polymeric material is water-insoluble or hydrophobic. For example and without limitation, in one aspect, the non-biodegradable matrix can comprise an ethylene vinyl acetate (EVA) co-polymer; polyethylene, polyethyl acrylate, and copolymers of ethylene and ethyl acrylate, and any combination thereof. In one aspect, the matrix is comprised of an ethylene vinyl acetate co-polymer having a relative percentage of vinyl acetate in the range of from 0% to approximately 60%, including additional vinyl acetate percentages as approximately 0%, 1%, 5%, 10%, 15%, 20%, 25%, 30%, 35%, 40%, 45%, 50%, 55%, and 60% and any range of percentages derived from these values. In still another aspect, the ethylene vinyl acetate co-polymer comprises approximately 28% vinyl acetate.

The hydrophilic permeant can comprise any chemical or biological material, compound, or composition suitable for administration by the conventional methods previously known in the art and/or by the methods taught in the present invention. To this end, the permeant can comprise any one or more components that would be desired to be administered transdermally. For example, the hydrophilic permeant can be selected from a bioactive agent, a filler, an anti-healing agent, an osmotic agent, and any other conventionally known additive suitable for providing or enhancing a desired transdermal delivery of a permeant. In one aspect, the hydrophilic permeant can account for approximately 20 weight % to approximately 80 weight % of the reservoir, including additional amounts as 25 weight %, 30 weight %, 35 weight %, 40 weight %, 45 weight %, 50 weight %, 55 weight %, 60 weight %, 65 weight %, 70 weight %, and 75 weight % of the reservoir, and including any range of weight percentages derived from these values.

In still another aspect, the bioactive agent can be present within the reservoir 104 as an undissolved anhydrous hydrophilic salt. To that end, as used herein, "hydrophilic salt" and similar terms include, without limitation, an ionic form of a bioactive agent, drug, or pharmaceutical agent, such as sodium, potassium, ammonium, trimethamine, or other cation salts thereof, sulfate or other anion salts thereof, acid addition salts of basic drugs, and base addition salts of acidic drugs. Illustrative examples of such salts include sodium diclofenac, sodium cromolyn, sodium acyclovir, sodium ampicillin, sodium warfarin, ketorolac tromethamine, amiloride HCl, ephedrine HCl, loxapine HCl, thiothixene HCl, trifluoperizine HCl, naltrexone HCl, naloxone HCl, nalbuphine HCl, buspirone HCl, bupriprion HCl, phenylephrine HCl, tolazoline HCl, chlorpheniramine maleate, phenylpropanolamine HCl, clonidine HCl, dextromethorphan HBr, metoprolol succinate, metoprolol tartrate, epinephrine bitartrate, ketotofin fumarate, atropine sulfate, fentanyl citrate, apomorphine sulfate, propranolol HCl, pindolol HCl, lidocaine HCl, tetracycline HCl, oxytetracycline HCl, tetracaine HCl, dibucaine HCl, terbutaline sulfate, scopolamine HBr, brompheniramine maleate and hydromorphone HCl.

In addition to one or more bioactive agents, the at least one permeant can also comprise a bio-compatible filler, which can comprise any one or more of an excipient, hydroscopic agent, osmotic agent, permeation enhancer, anti-healing agent, anti-clotting agent, anti-inflammatory, anti-microbial agents, re-epitheliating inhibitory agent, nitrous oxide production inhibitory agent, melanogenesis inhibitory agents, dosing agent, and the like. In one aspect, the bio-compatible filler can account for approximately 20 weight % to approximately 80 weight % of the reservoir, including additional amounts as 25 weight %, 30 weight %, 35 weight %, 40 weight %, 45 weight %, 50 weight %, 55 weight %, 60 weight %, 65 weight %, 70 weight %, and 75 weight % of the reservoir, and including any range of weight percentages derived from these values.

Further, as used herein, an anti-healing agent can include, for example, anticoagulants, anti-inflammatory agents, agents that inhibit cellular migration, re-epithelization inhibiting agents, and osmotic agents. Suitable anticoagulants can comprise, for example, heparin having a molecular weight from 3,000 to 12,000 daltons, pentosan polysulfate, citric acid, citrate salts, EDTA, and dextrans having a molecular weight from 2,000 to 10,000 daltons. Suitable anti-inflammatory agents can comprise, for example, hydrocortisone sodium phosphate, betamethasone sodium phosphate, and triamcinolone sodium phosphate. Suitable agents that inhibit cellular migration can comprise, for example, laminin and/or its related peptides.

In one example of the reservoir 104, the at least one hydrophilic permeant is typically disposed or otherwise loaded within the non-biodegradable matrix. To this end, in an exemplary aspect, the delivery reservoir can be configured such that it has a bottom surface that defines a plurality of conduits therein. According to this aspect, the undissolved hydrophilic permeant can be disposed therein at least a portion of the plurality of conduits of the matrix. As such, the exemplified delivery reservoir 104 is adapted to use subcutaneous fluid exuded from the skin to dissolve or suspend at least a portion of the permeant disposed within the matrix to enable diffusion or transport of the permeant into the deeper layers of the skin.

Various mechanisms of transport can effect the dispersion and movement of the undissolved permeant from the reservoir into the skin tissues. In general, but not exclusively, a permeant disposed within the matrix becomes available to the organism upon release by leaving the micro-particulate form and typically going into solution or suspension. Once in solution or suspension, diffusion can provide the transport mechanism for the micro-particulate permeant via the treated outer layers and into or through the viable layers of the skin and into the subject. As the process continues over time, the voids formed by the permeant that leaves the reservoir and moves into the skin form channels penetrating into the body of the reservoir thereby providing additional access to more permeant than was initially present at the surface of the reservoir. Accordingly, by placing the reservoir 104 in communication with at least one formed pathway through the skin layer of a subject, subcutaneous fluid can provide an effective amount or level of hydration to the reservoir to dissolve or suspend the permeant. As such, a relatively high concentration of permeant in solution or suspension can be provided that is also in communication to the viable tissue layers of the skin.

Figure 17:
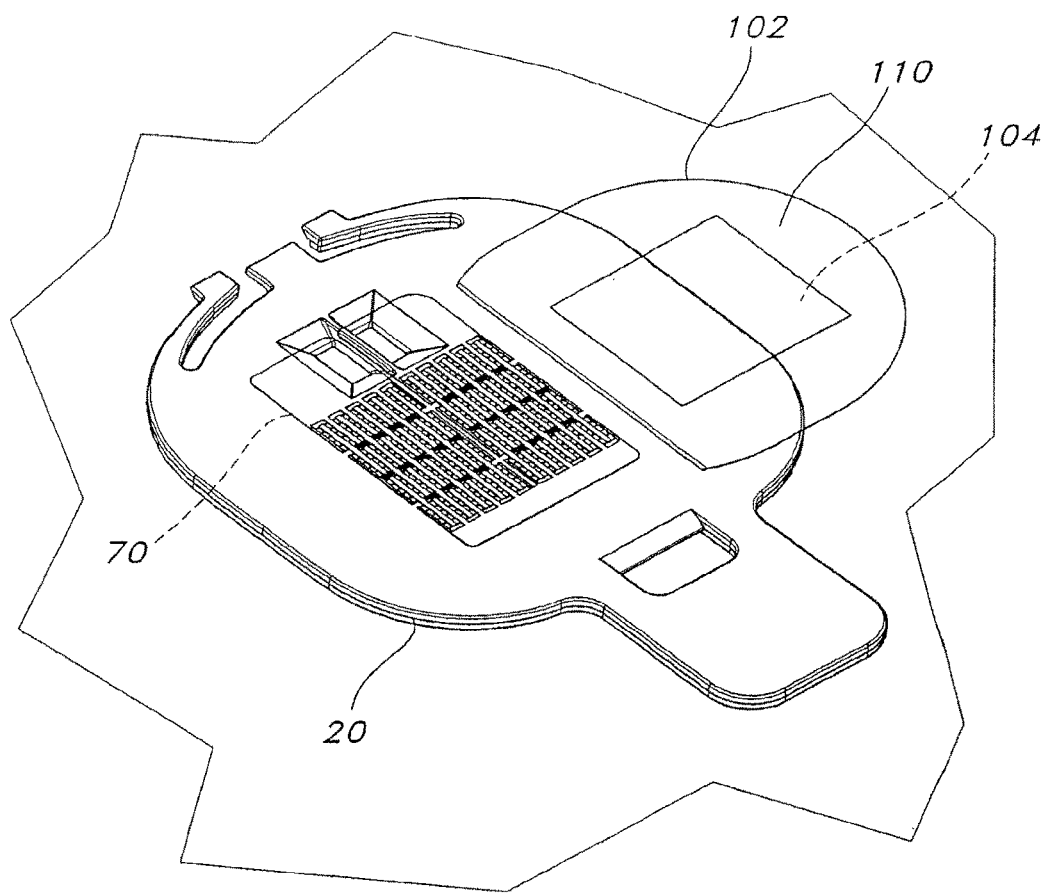
FIG. 17 is a perspective schematic view of the transdermal permeant delivery system of FIG. 1 shown connected to the skin of the subject prior to the poration of the skin of the subject.
Figure 18:
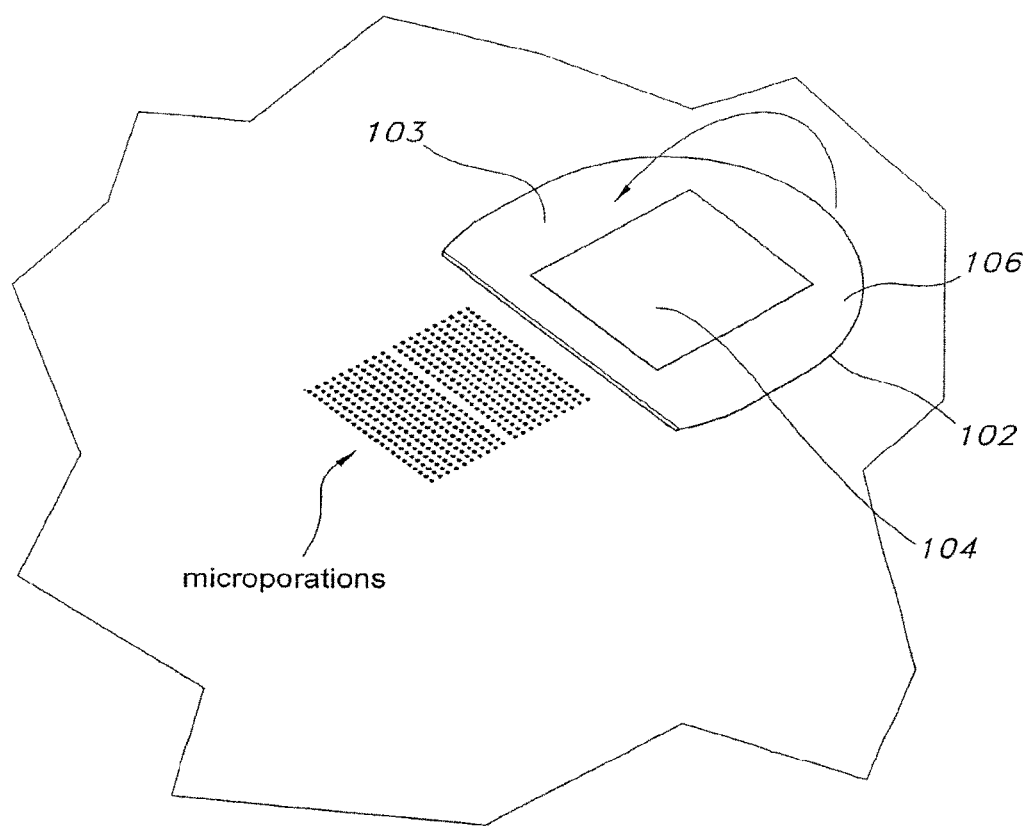
FIG. 18 is a perspective schematic view of the transdermal permeant delivery system showing the transdermal patch being separated from a portion of the transdermal permeant delivery system after poration of the subject's skin.
Figure 19:
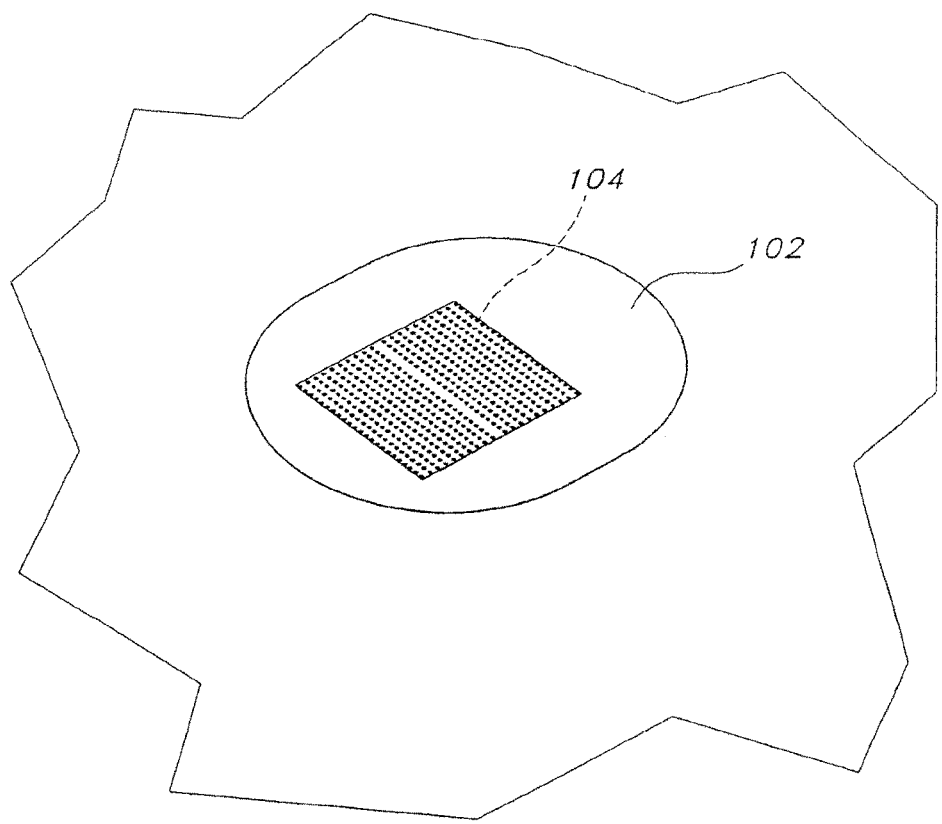
FIG. 19 is a perspective schematic view of the transdermal patch positioned in registration with the porated area of the subject's skin.

Referring now to FIGS. 17-19, an exemplified aspect of the transdermal permeant delivery system is shown connected to the skin of the subject prior to the poration event. Here, the second release liner has been removed to expose a portion of the skin adhesive layer of the patch, which is shown in adhesive contact with the tissue membrane of the subject. The applicator is subsequently actuated so that poration of the area of the tissue membrane that underlies the poration area of the substrate occurs. In one exemplified aspect, the actuation of the applicator causes an electrical stimulus to be delivered to the means for forming at least one micropore to cause the ablation of the underlying tissue membrane. For example, the electrical stimulus can be delivered to the filaments of the filament array to cause resistive heating thereof and thermal ablation of the underlying tissue membrane. In a further aspect, if used, the actuation of the applicator can initiate the source of vacuum such that a vacuum is delivered to the poration area via the conduit and associated channels. One would appreciate that the vacuum provided would act to draw the tissue membrane into intimate contact with the means for forming the at least one micropore mounted therein the poration area, such as, for example, the exposed portion of the filament array and would additionally serve to help secure the applicator to the tissue membrane during the course of the microporation event.

After the micropores are formed, and as shown in FIG. 18, the transdermal patch is separated from a portion of the transdermal porator system. In operation, as the applicator is removed, the substrate remains mounted to the interface of the applicator and the patch separates from the first release liner. In this configuration, the patch is secured to the tissue membrane by that portion of the backing layer that had been previously secured to the tissue membrane after the second release liner had been removed. The now exposed portions of the backing layer and the reservoir face away from the underlying tissue membrane and are positioned such that the reservoir is registered about the fold with the microporated area of the tissue membrane. Referring now to FIG. 19, the patch is folded over with respect to the fold such that the transdermal patch is positioned in registration with the microporated area of the subject's skin. After the patch is pressed into place, all other components of the system that may remain are removed to leave only the patch with the reservoir. As one will appreciate, the permeant then diffuses from the reservoir through the micropores in the porated area of the tissue into the body over a period of time. This period of time may be minutes or days as appropriate for the specific permeant and use indication for the permeant.

Figure 22:
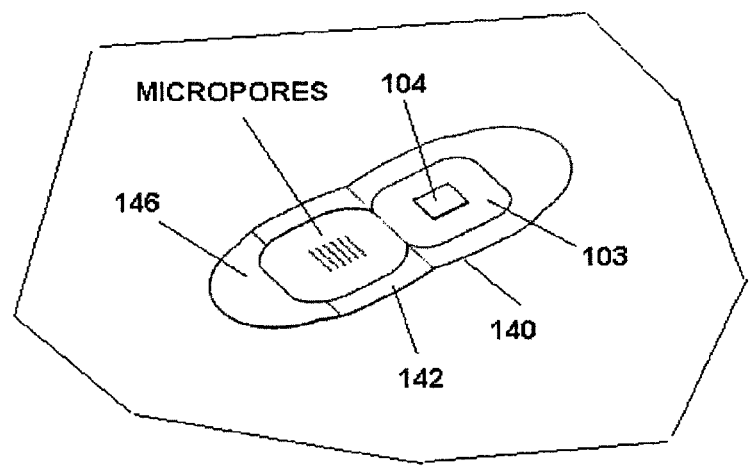
FIG. 22 is a perspective schematic view of the transdermal permeant delivery system of FIG. 21 showing the transdermal patch after being separated from a portion of the transdermal permeant delivery system after poration of the subject's skin.
Figure 23:
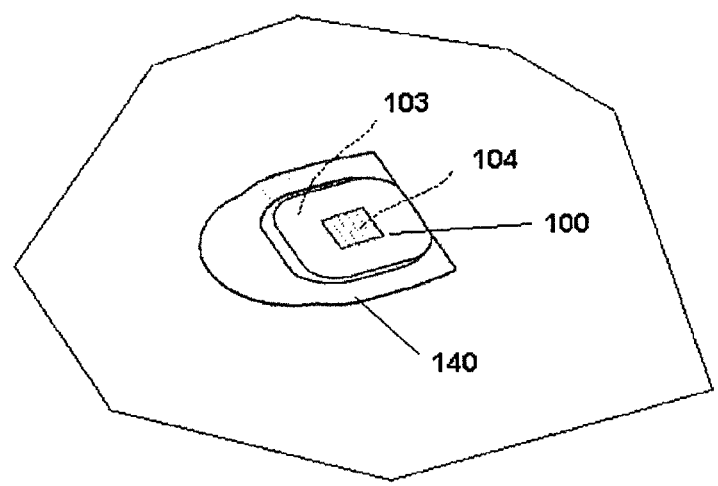
FIG. 23 is a perspective schematic view of the transdermal permeant delivery system showing the transdermal patch after the reservoir of the patch is folded into registration with the formed micropores.
Figure 24:
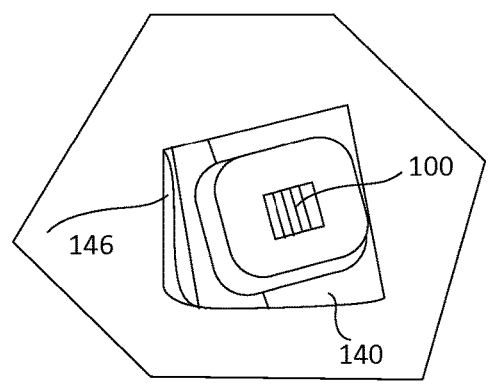
FIG. 24 is a perspective schematic view of the transdermal permeant delivery system showing removable portions of the transdermal permeant delivery system being separated from the transdermal patch.

Referring now to FIGS. 22-24, an exemplified aspect of the transdermal permeant delivery system is shown connected to the skin of the subject. Here, after the micropores are formed, and as shown in FIG. 22, the transdermal patch is separated from a portion of the transdermal porator system. In operation, as the applicator is removed, the substrate remains mounted to the interface of the applicator and the patch separates from the first release liner. In this configuration, the skin adhesive layer is secured to the tissue membrane and the patch is positioned in registration with the formed micropores via the patch backing film. Thus, the now exposed portions of the backing layer and the reservoir of the patch face away from the underlying tissue membrane and are positioned such that the reservoir is registered about the fold with the microporated area of the tissue membrane. Referring now to FIG. 23, the patch backing film is folded over such that the patch is folded with respect to a fold such that the transdermal patch is positioned in registration with the microporated area of the subject's skin. After the patch is pressed into place, and as shown in FIG. 24, the patch backing film and all other components of the system that may remain are removed to leave only the patch with the reservoir in contact with the tissue membrane. As one will appreciate, the permeant then diffuses from the reservoir through the micropores in the porated area of the tissue into the body over a period of time. As noted above, this period of time may be minutes or days as appropriate for the specific permeant and use indication for the permeant.

It is of course contemplated that the shapes of the patch that are exemplified in the figures are merely representative shapes and are not meant to be limiting. The overall concept of the system is to provide an alignment or registration mechanism which facilitates the application of the means for forming at least one micropore and then the subsequent step of applying a permeant reservoir patch over the area in which the micropores are formed. As noted above, the means for forming at least one micropore can comprise, without limitation, thermal, mechanical, optical, chemical, electrical or acoustical ablation means.

In a further aspect, the present inventive subject matter also includes a method for using such a device for administering a permeant to a patient in need thereof. The design of the present transdermal delivery system ensures proper registration of the reservoir of the patch over the porated tissue membrane after application and actuation of a filament array. From the user's perspective, after the substrate is mounted to the applicator and the second release liner is removed, what is actually multiple steps becomes a single step of applying the applicator, actuating the applicator to form the micropores in the underlying tissue, removing the applicator (which includes removing the substrate and the first release liner to expose the backing layer of the patch), then folding the patch over in place to position the reservoir of the patch in registration with the porated area of the tissue membrane, the set of operations being so intimately linked that they quickly become a single process in the minds eye.

It is contemplated that the substrate and patch, positioned in the connected position with the second release liner attached thereto can be packaged individually in a single foil pack. Further, it is contemplated that this assembly can be formed and sterilized if needed, then filled with the selected permeant (aseptically if needed) prior to being sealed into the hermetic foil pack.

In one aspect and as described above, the interface to the applicator is configured to allow to applicator 20 to selectively deliver sufficient electrical energy to create micropores in the outer layers of the patient's skin. As described herein and for example and without limitation, the formed micropores can be created for the purpose of enabling the transdermal delivery of drugs or vaccines from a patch that can be selectively placed over the micropores.

In one aspect the applicator 20 and the interface 30 is configured to support multiple filament array sizes. For example and without limitation, the applicator can support 1, 2, 3, 4, or more filament array sizes, such as, for example, 1, 2, 4 and 8 cm$^2$ array sizes. In a further aspect, the applicator 20 can be configured to detect the size of the filament array of the attached substrate and can automatically configure itself for the detected size of the filament array. The following example is described with respect to a filament array embodiment of the means for forming at least one micropore, but one skilled in the art will appreciate that it is contemplated that the described modalities could be used for the selected modality.

In a further aspect, the applicator 20 can be configured to turn on or power up upon the insertion of the substrate onto the interface of the applicator. In another aspect, the applicator 20 can be configured to initiate application of vacuum pressure when the substrate is mounted thereon the interface of the applicator. In this aspect, the application of vacuum pressure can be initiated automatically when the applicator determines that it is properly configured. In another aspect, it is contemplated that the applicator could have a power button to initiate power up of the applicator. However, optionally, it is contemplated that power up of the applicator can be initiated by insertion of the substrate 40, which "wakes-up" the applicator, which can then go through a series of self-tests, such as, for example and without limitation, battery voltage tests. In one aspect, if the applicator 20 passes the self-tests, a power light is illuminated and the applicator internally prepares for an activation sequence. In one aspect, the activation sequence will charge high voltage capacitors, for example up to about ~230 volts. This voltage is set by hardware and, for example and without limitation, can go up to 330 volts.

In operation, the user mounts the substrate into position on the application, which engages the electrical contacts when, for example, the substrate is snapped down into it's final mounted position. In one aspect, the applicator 20 can continue to charge the high-voltage capacitors during this time. In a further aspect, when the capacitors are fully charged, a ready light can be illuminated. In another aspect, upon illumination of the ready light, the applicator can initiate a vacuum pulsing sequence. In a further aspect, the applicator can further comprise a low battery indication and an error indication.

Figure 29:
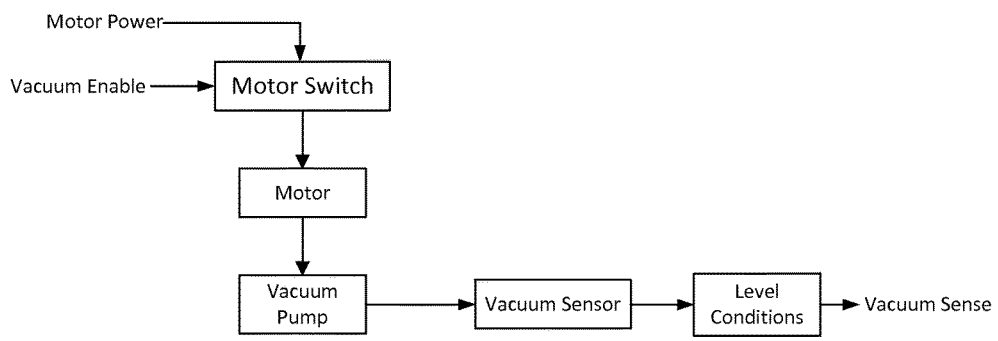
FIG. 29 shows an exemplary schematic of a vacuum circuit block diagram.

In one aspect, the user removes the release liner protecting the adhesive surrounding the filament array and positions the applicator on an appropriate skin site and the vacuum pump continues to pulse until a nominal vacuum is achieved, such as, for example and not meant to be limiting, about ten inches Hg vacuum. An exemplary schematic of the vacuum circuit is shown in FIG. 29. Once an adequate vacuum seal is established, the applicator can be configured to send at least one current pulse to the filament array. As noted herein, the filaments provide a thermal pulse of energy to the skin, which creates micropores in the skin. As exemplary illustrated herein, the user then removes the applicator and substrate and folds over the registered patch onto the microporated portion of the skin.

Figure 25:
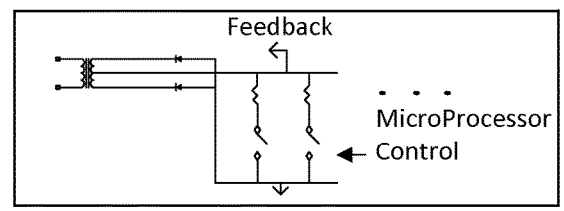
FIG. 25 shows an exemplary schematic of an applicator circuit.
Figure 25:
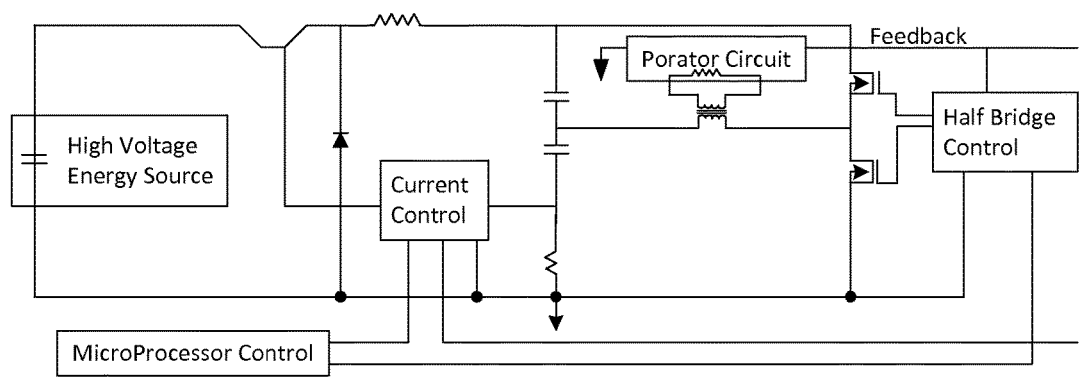

In an exemplary embodiment, and as shown in FIG. 25, the applicator electronics can be exemplarily broken down into two functional blocks—a controller or microprocessor control circuit and the applicator power delivery circuits. In one aspect, the filament array can require, for example and without limitation, approximately 120 amps for a few milliseconds. However, it is contemplated that other current levels can be optionally selected. For example, as one skilled in the art will appreciate, depending on the filament array size and use characteristics, the current delivery operating point may utilize pulse-width modulation to regulate the effective energy delivered to the filament array. In one aspect, peak current delivery can influence warm-up time of the filament array when applied to the skin. Consequently, an ensemble of pulse times in conjunction with controlled current delivery can be used. In a further aspect, an additional 'mode' contact can be added to assure that the applicator recognizes the designated filament array size and rejects combinations of contacts resulting from open electrical contacts.

In one embodiment and referring now to the circuit schematic illustrated in FIG. 25, a Buck converter in a constant current mode can be utilized. Buffer capacitors store the current-source energy and feed a half-bridge transforming function. In this aspect, the secondary of the transformer is configured to provide energy to the filament array circuit. One skilled in the art will appreciate that the exemplified control blocks are commercially-available integrated circuits and the whole circuit is enabled under microprocessor control. The exemplified circuit supports several possible filament array circuits including, for example, switched banks.

Figure 26:
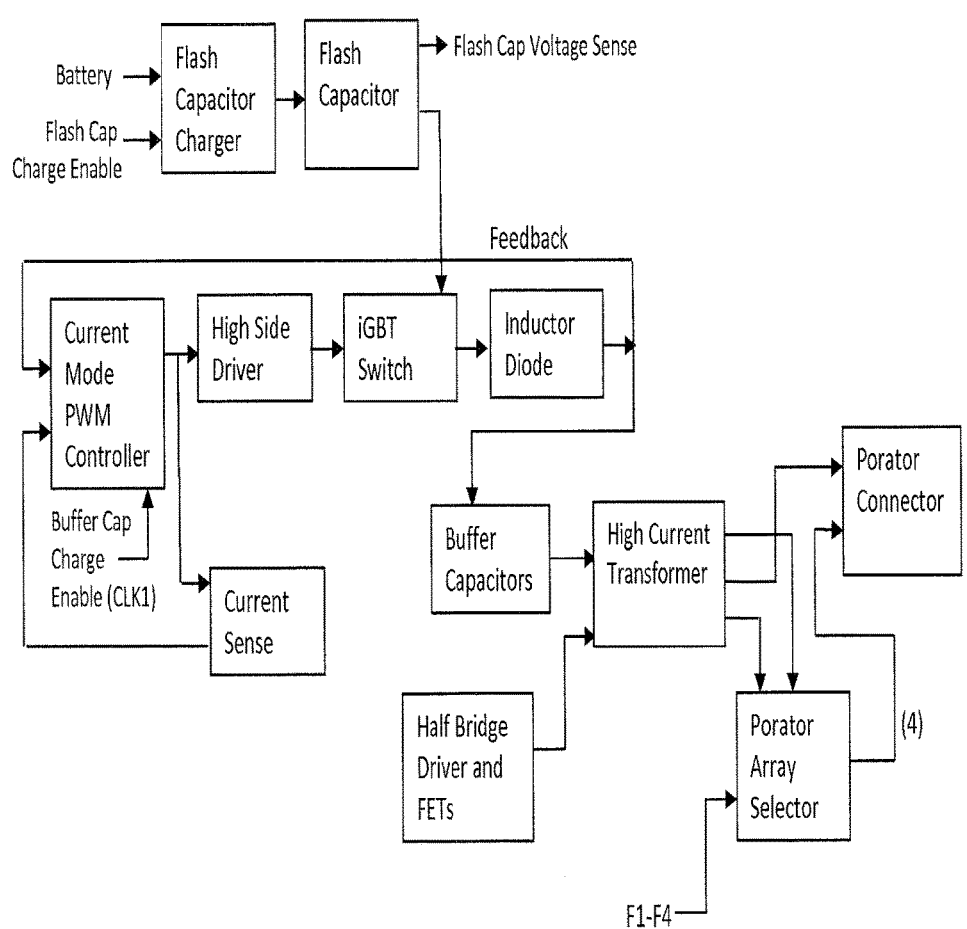
FIG. 26 shows an exemplary schematic of an exemplary power circuit for the applicator.
Figure 27:
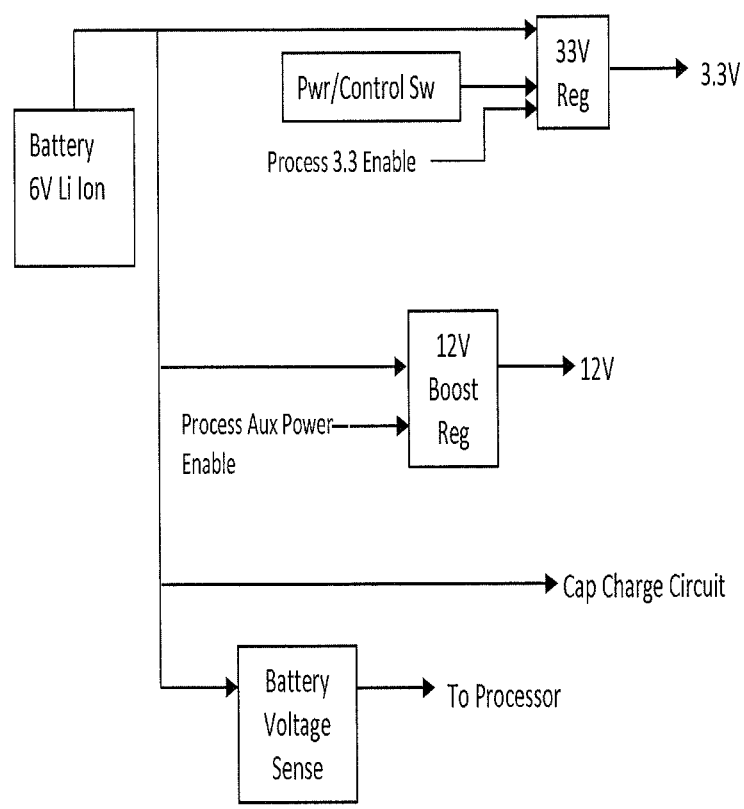
FIG. 27 shows an exemplary schematic of a bias power block diagram.

Referring now to FIG. 26, a schematic of an exemplary power circuit is illustrated. As mentioned above, energy can be first stored as high voltage in at least one flash capacitor. Once the capacitor(s) have reached their desired voltage, the high current poration sequence can begin. In one aspect, a constant-current source pulls a steady current out of the high-voltage capacitors and temporarily stores this energy in at least one sequential buffer capacitor. In another aspect, a half-bridge switch-mode converter can then perform an impedance matching function—transforming high-voltage and intermediate current energy into very high-current and low voltage suitable for driving the filament array. In one example and not meant to be limiting, the secondary currents can be about 120 amps at between about 5-10 volts.

In a further aspect, and as one skilled in the art will appreciate, a power source, regulation and distribution methods are required. In the applicator 20, it is contemplated that all of the required internal energy can be sourced by two 3 Volt lithium batteries, which are easily replaced by the use.

As noted above, the applicator 20 can be configured so that the "insertion" of a substrate into the interface of the applicator "wakes up" the microprocessor of the applicator. Subsequently, the applicator can latch up the 3.3 Volt regulator. In this aspect, the microprocessor unlatches this control circuit when the applicator has served its intended purpose or, alternatively, if a software generated time-out indicates that the applicator is idle. Optionally, certain error conditions, such as, for example and without limitation, a dead battery and/or software check-sum faults can also result in errors that will cause the unit to shut down.

Figure 28:
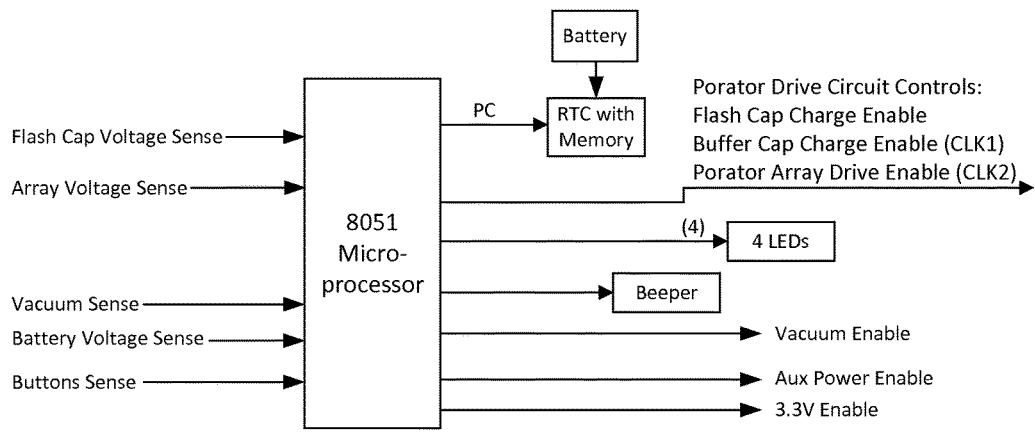
FIG. 28 shows an exemplary schematic of a microprocessor block diagram.

An exemplary schematic of the microprocessor block diagram is shown in FIG. 28. The microprocessor exemplarily supports several functions such as, without limitation: internal power control, user interface (buttons, lights, and beeper), applicator power control, vacuum, development interface, manufacturing interface and diagnostics. The applicator driving software is configured to support many system interfaces and defines interaction between the applicator (including hardware and software) and an external function. In a further aspect, the applicator can be configured to monitor the application power (via a feedback circuit) and will real-time adjust the application energy, i.e., the applied pulse modulation. This aspect adjusts for variations in filament array electrical impedance.

Identified system interfaces can comprise, without limitation: functional test, programming interface and user interface. In one aspect, the functional test executes if the serial interface is attached and enabled and initiated. The test starts after startup diagnostics when the test user requests initiation. In one example, the functional test can utilize the beeper to indicate the result of the functional test where tone frequency indicates a 1 (high frequency tone) or 0 (low frequency tone) and position dependence in binary format identifies specific module test pass/fail results. Result codes are also displayed through the serial interface. Specific test module details and place value dependence are described later. For any functional test module result that indicates a failure, the unit will generate a FT fail tone while flashing test codes. If all functional test modules pass, the processor-controlled LEDs will flash times while the unit generates a FT pass tone sequence (4 high frequency tones). Functional test modules can include: [0143] 1. Timer Test—checks timer function by verifying timer is incrementing. [0144] 2. Memory Test—verify memory function by writing and reading from selected locations in memory. [0145] 3. Charge Test—verify charge function by charging system to 100V within 1 second. [0146] 4. Vacuum System Test—verify that vacuum threshold can be reached to start activation. [0147] 5. ADC Test—verify function of ADC circuit and 3.3V supply by reading AVREF. Result should be within 5% of 2.5 Volts [0148] 6. PWM Test—verify function of PWM by checking for completion of programmed tone. [0149] 7. Battery Test—verify battery check circuit by confirming that AVREF voltage is between 2.25 and 3.35 volts and battery voltage is within 5.8-7.0 volts. [0150] 8. Watchdog Test—verify watchdog timer by setting error code to functional test mode and allowing timeout. [0151] 9. Parameter Test—verify that parameter values match secondary location. [0152] 10. Checksum Test—verify program integrity by comparing generated 16 bit checksum to stored value. [0153] 11. CLK test generates a 1 millisecond pulse on CLK1 followed by a 1 millisecond pulse on CLK2. Test verification will be performed prior to final assembly. [0154] 12. Control and Status Signals Loopback test—Verify function of main to secondary control and status signals if in Loopback Test mode.

The microprocessor can exemplarily use a 2 wire interface for programming internal flash memory. In one aspect, the interface becomes active when the microprocessor senses the programming interface. One skilled in the art will appreciate that when the programming interface is active the processor is under control of the programming interface.

In one example the applicator user interface can comprise a plurality of processor controlled LEDs, a hardware controlled LED, a multi-tone speaker, and a Power/Activate button. The processor controlled LEDs can be configured to indicate battery status, error status, and/or activation readiness. In one aspect, there can be one spare processor controlled LED. In this aspect, the hardware controlled LED can be configured to indicate system power status. The beeper can be used to signify errors, good events, bad events, and/or information events.

In a further aspect, the applicator functions can be exemplarily implemented through control software that can be broken into tasks to facilitate a modular approach. For example, the tasks can be broken down to the following: Main—software entry point and top level task sequence. Initialization—device initialization and startup diagnostics. Monitoring-Prepare device for activation. Activation—checks for valid activation conditions and controls delivery of energy to porator. Shutdown—updates error status and powers down device.

The Applicator software can contain additional modular units to interface to hardware and internal functions such as, for example and without limitation: User Interface (UI); Functional Test; Error Handler; Analog to Digital Conversion (ADC); Timers; Port I/O; and/or Programmable Counter (PCA).

Figure 30:
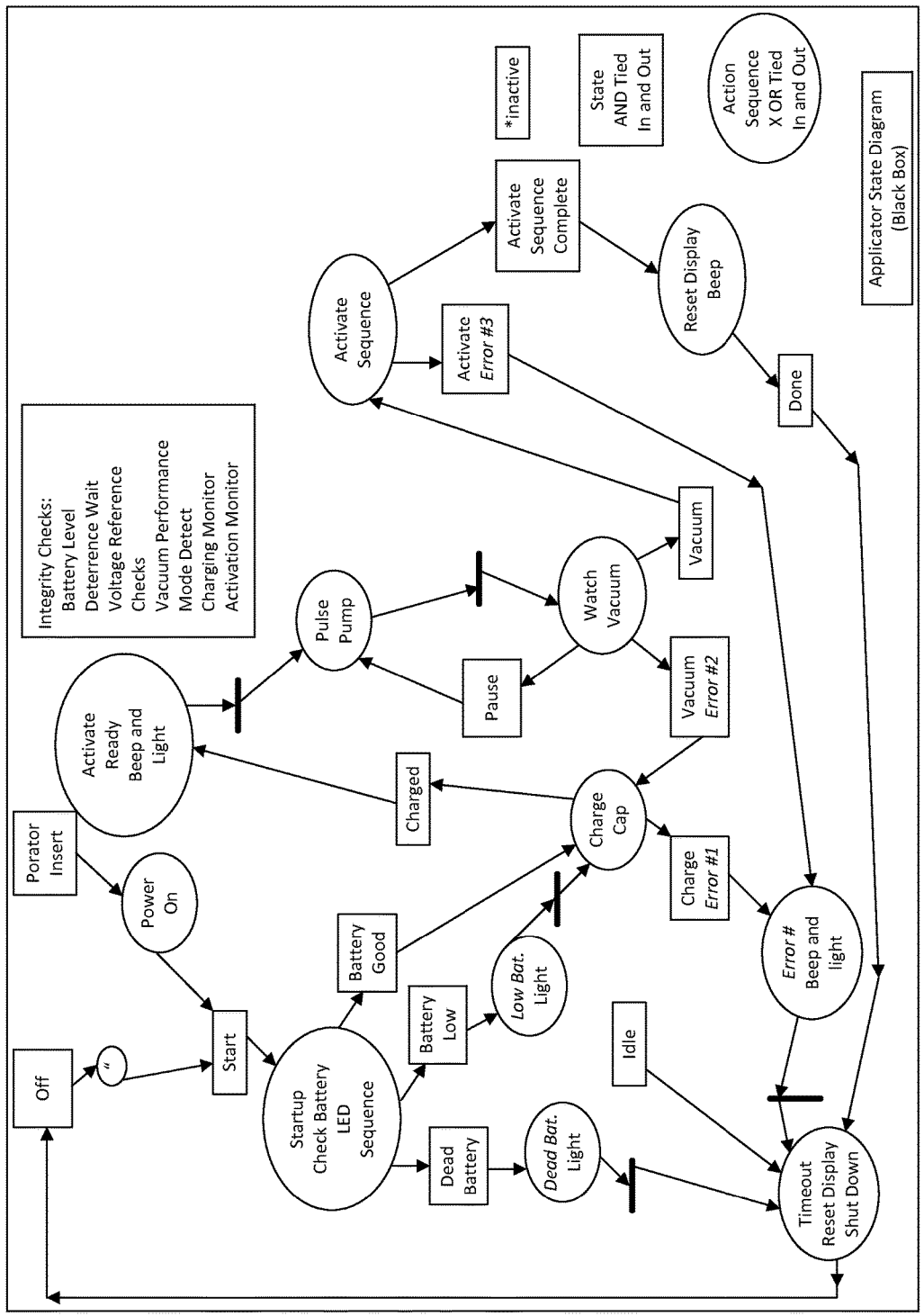
FIG. 30 schematically illustrates an exemplary a top level behavioral flow diagram of the applicator.

FIG. 30 schematically illustrates an exemplary a top level behavioral flow diagram of the software of the applicator.

The invention claimed is:

1. A method of transdermal monitoring, comprising steps of:
   forming at least one micropore in a tissue membrane by a microporation device, while delivering a vacuum to draw the tissue membrane; and
   monitoring a subcutaneous fluid via the at least one micropore by a monitoring device;
   wherein
   the microporation device comprising:
   a vacuum source to generate the vacuum;
   a disposable substrate
      defining a poration area and
      having an upper substrate surface, a lower substrate surface, a conduit that extends between the upper substrate surface and the lower substrate surface;
   at least one channel disposed on the upper substrate surface and in fluid communication with the conduit so that the vacuum, is delivered to the poration area via the conduit and the at least one channel;
   a means for forming at least one micropore in the tissue membrane, wherein said means is mounted on the substrate, and wherein at least a portion of the means is positioned within the poration area; and
   wherein the vacuum acts to draw the tissue membrane into contact with the means for forming at least one micropore, when the microporation device acts to form the at least one micropore in the tissue membrane.

2. The method of transdermal monitoring according to claim 1, wherein the monitoring device comprises a sensor for measuring a characteristic of the subcutaneous fluid.

3. The method of transdermal monitoring according to claim 2, wherein the sensor is for determining a concentration of an analyte in the subcutaneous fluid.

4. The method of transdermal monitoring according to claim 3, wherein the sensor is a glucose sensor.

5. A transdermal monitoring system, comprising:
   a microporation device adapted to form at least one micropore in a tissue membrane, while delivering a vacuum to draw the tissue membrane; and
   a monitoring device adapted to monitor a subcutaneous fluid via the at least one micropore;
   wherein
   the microporation device comprising:
   a vacuum source to generate the vacuum;
   a disposable substrate
      defining a poration area and
      having an upper substrate surface, a lower substrate surface, a conduit that extends between the upper substrate surface and the lower substrate surface;
   at least one channel disposed on the upper substrate surface and in fluid communication with the conduit so that the vacuum is delivered to the poration area via the conduit and the at least one channel;
   a means for forming at least one micropore in the tissue membrane, wherein said means is mounted on the substrate, and wherein at least a portion of the means is positioned within the poration area; and
   wherein the vacuum acts to draw the tissue membrane into contact with the means for forming at least one micropore, when the microporation device acts to form the at least one micropore in the tissue membrane.

6. The transdermal monitoring system according to claim 1, wherein the monitoring device comprises a sensor for measuring a characteristic of the subcutaneous fluid.

7. The transdermal monitoring system according to claim 6, wherein the sensor is for determining a concentration of an analyte in the subcutaneous fluid.

8. The transdermal monitoring system according to claim 7, wherein the sensor is a glucose sensor.

* * * * *